US005925376A

United States Patent [19]
Heng

[11] Patent Number: 5,925,376
[45] Date of Patent: Jul. 20, 1999

[54] METHOD FOR TREATING PSORIASIS USING SELECTED PHOSPHORYLASE KINASE INHIBITOR AND ADDITIONAL COMPOUNDS

[76] Inventor: Madalene C. Y. Heng, 17632 Vincennes St., Northridge, Calif. 91325

[21] Appl. No.: 08/518,991

[22] Filed: Aug. 24, 1995

Related U.S. Application Data

[63] Continuation-in-part of application No. 08/179,167, Jan. 10, 1994, abandoned.
[51] Int. Cl.$^6$ .............................. A61K 9/20; A61K 9/06
[52] U.S. Cl. .................... 424/451; 424/464; 514/886; 514/863; 514/944; 514/937; 514/962; 514/969; 514/679
[58] Field of Search ................................ 424/472, 195.1, 424/451, 464; 514/731, 886, 863, 944, 937, 962, 969, 679

[56] References Cited

U.S. PATENT DOCUMENTS 5,401,777  3/1995  Ammon et al. ........................ 514/731

FOREIGN PATENT DOCUMENTS 4137540   5/1993   Germany .
93/23061  11/1993  WIPO .

OTHER PUBLICATIONS

N.J. Lowe et al., "Cutaneous Polyamines in Psoriasis," *Br. J. Dermatol.* 107:21–26 (1982).
S. Forster et al., "Characterization and Activity of Phospholipase A$_2$ in Normal Human Epidermis and in Lesion–Free Epidermis of Patients with Psoriasis or Eczema," *Br. J. Dermatol.* 112:135–147 (1985).
R. Marks, "Epidermal Activity in the Involved and Uninvolved Skin of Patients with Psoriasis," *Br. J. Dermatol.* 98:399–404 (1978).
E.M. Farber et al., "Role of Trauma in Isomorphic Response in Psoriasis," *Arch. Dermatol.* 91:246–251 (1965).
L.F. Fajardo et al., "Dual Role of Tumor Necrosis Factor–α in Angiogenesis," *Am. J. Path.* 140:539–544 (1992).
G.D. Weinstein & J.L. McCullough, "Cytokinesis in Diseases of Epidermal Hyperplasia," *Annu. Rev. Med.* 24:345–352 (1973).
E.G. Krebs & J.A. Beavo, "Phosphorylation–Dephosphorylation of Enzymes," *Annu. Rev. Biochem.* 48:923–959 (1979).
E.J. Van Scott & T.M. Ekel, "Kinetics of Hyperplasia in Psoriasis," *Arch. Dermatol.* 88:373–381 (1969).
H. Roelfzema et al., "Studies on the Plasma Membrane of Normal and Psoriatic Keratinocytes. 4. Characterization of Glycoconjugates," *Br. J. Dermatol.* 105:509–516 (1981).
S. Gelfant, "The Cell Cycle in Psoriasis: a Reappraisal," *Br. J. Dermatol.* 95:577–590 (1976).
C. Cochet & E.M. Chambaz, "Polyamine–Mediated Protein Phosphorylations: A Possible Target for Intracellular Polyamine Action," *Mol. Cell. Endocrinol.* 30:247–266 (1983).

J.J. Davidson et al., "cDNA Cloning of a Liver Isoform of the Phosphorylase Kinase α Subunit and Mapping of the Gene to Xp22.2–p22.1, the Region of Human X–Linked Liver Glycogenesis," *Proc. Natl. Acad. Sci. USA* 89:2096–2100 (1992).
P. Cohen, "The Role of Protein Phosphorylation in Neural and Hormonal Control of Cellular Activity," *Nature* 296:613–620 (1982).
M. Fräter–Schröder et al., "Tumor Necrosis Factor Type α, a Potent Inhibitor of Endothelial Cell Growth in vitro, is Angiogenic in vivo," *Proc. Natl. Acad. Sci. USA* 84:5277–5281 (1987).
D. Brion et al., "Deficiency of Cyclic AMP–Dependent Protein Kinases in Human Psoriasis," *Proc. Natl. Acad. Sci. USA* 83:5272–5276 (1986).
S. Hammarström et al., "Increased Concentrations of Non-esterified Arachidonic Acid, 12L–Hydroxy–5,8,10,14–Eicosatetraenoic Acid, Prostaglandin E$_2$, and Prostaglandin F$_{2\alpha}$ in Epidermis of Psoriasis," *Proc. Natl. Acad. Sci. USA* 72:5130–5134 (1975).
C.L. Marcelo & J.J. Voorhees, "Cyclic Nucleotides and the Control of Psoriatic Cell Function," *Adv. Cyclic Nucleotide Res.* 12:129–137 (1980).
H. Hennings et al., "Calcium Regulation of Growth and Differentiation of Mouse Epidermal Cells in Culture," *Cell* 19:245–254 (1980).
J.G. Chafouleas et al., "Changes in Calmodulin and its mRNA Accompany Reentry of Quiescent (G0) Cells Into the Cell Cycle," *Cell* 36:73–81 (1984).
S.T. Boyce & R.G. Ham, "Calcium–Regulated Differentiation of Normal Human Epidermal Keratinocytes in Chemically Defined Clonal Culture and Serum–Free Serial Culture," *J. Invest. Dermatol.* 81:33s–40s (1983).

(List continued on next page.)

*Primary Examiner*—Raj Bawa
*Attorney, Agent, or Firm*—Merchant, Gould, Smith, Edell, Welter & Schmidt

[57] ABSTRACT

An improved method of treating psoriasis involves controlling the enhanced proliferation and terminal differentiation of psoriatic epidermis through the activity of epidermal phosphorylase kinase. In general, the method involves contacting psoriatic epidermal cells with a combination of substances affecting the activity of phosphorylase kinase. The combination can be: (1) a calmodulin inhibitor together with a stimulator of cAMP-dependent protein kinase II, (2) a calmodulin inhibitor together with a calcium channel blocker; (3) a stimulator of cAMP-dependent protein kinase II together with a calcium channel blocker; or (4) a calmodulin inhibitor together with a calcium channel blocker and a stimulator of cAMP-dependent protein kinase II. Alternatively, a selective phosphorylase kinase inhibitor such as curcumin can be administered, alone or with an agent such as vitamin D$_3$ or an analogue thereof, etretinate, diltiazem, or anthralin. The invention also includes pharmaceutical compositions.

5 Claims, 13 Drawing Sheets

OTHER PUBLICATIONS

B.A. Dale et al., "Identification of Filaggrin in Cultured Mouse Keratinocytes and its Regulation by Calcium," *J. Invest. Dermatol.* 81:90s–95s (1983).

G.K. Menon et al., "Ionic Calcium Reservoirs in the Malian Epidermis: Ultrastructural Localization by Ion–Capture Cytochemistry," *J. Invest. Dermatol.* 84:508–512 (1985).

J.D. Zieske & I.A. Bernstein, "Modification of Cell Surface Glycoprotein: Addition of Fucosyl Residues During Epidermal Differentiation," *J. Cell Biol.* 95:626–631 (1982).

W.F.G. Tucker et al., "Biologically Active Calmodulin Levels Are Elevated in Both Involved and Uninvolved Epidermis in Psoriasis," *J. Invest. Dermatol.* 82:298–299 (1984).

R.P. Weinberger & J.A.P. Rostas, "Effect of Zinc on Calmodulin–Stimulated Protein Kinase II and Protein Phosphorylation in Rat Cerebral Cortex," *J. Neurochem.* 57:605–614 (1991).

N.J. Donato et al., "Tumor Necrosis Factor Regulates Tyrosine Phosphorylation on Epidermal Growth Factor Receptors in A431 Carcinoma Cells: Evidence for a Distinct Mechanism," *Cell Growth & Different.* 3:259–268 (1992).

M.C.Y. Heng et al., "The Sequence of Events in Psoriatic Plaque Formation After Tape–Stripping," *Br. J. Dermatol.* 112:517–532 (1985).

M.C.Y. Heng et al., "High Endothelial Venules in Involved and Uninvolved Psoriatic Skin: Recognition by Homing Receptors on Cytotoxic T Lymphocytes," *Br. J. Dermatol.* 118:315–326 (1988).

M.K. Heng et al., "Reciprocity Between Tissue Calmodulin and cAMP Levels: Modulation by Excess Zinc," *Br. J. Dermatol.* 129:280–285 (1993).

M.C.Y. Heng et al., "Electron Microscopic and Immunocytochemical Studies of the Sequence of Events in Psoriatic Plaque Formation Following Tape–Stripping," *Br. J. Dermatol.* 125:548–556 (1991).

M.C.Y. Heng et al., "Expression of the L–Fucose Moiety on Epidermal Keratinocytes in Psoriasis Induced by the Koebner Phenomenon: A Sequential Study," *Br. J. Dermatol.* 126:575–581 (1992).

C. E. M. Griffiths et al., "Characterization of Intercellular Adhesion Molecule–1 and HLA–DR Expression in Normal and Inflamed Skin: Modulation by Recombinant Gamma Interferon and Tumor Necrosis Factor," *J. Am. Acad. Dermatol.* 20:617–629 (1989).

Bosman, B. (1994). *Skin Pharmacology* 7(6):324–334.

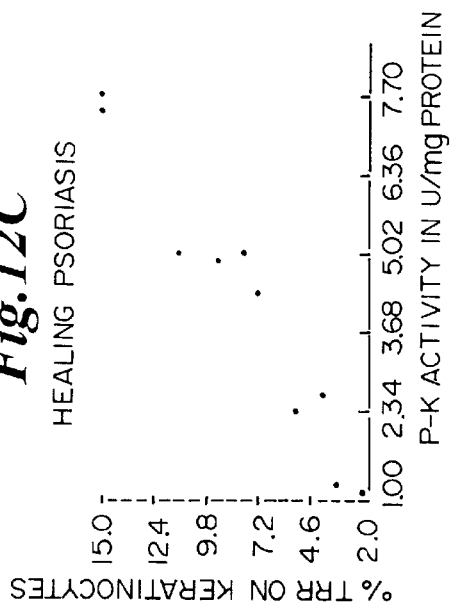
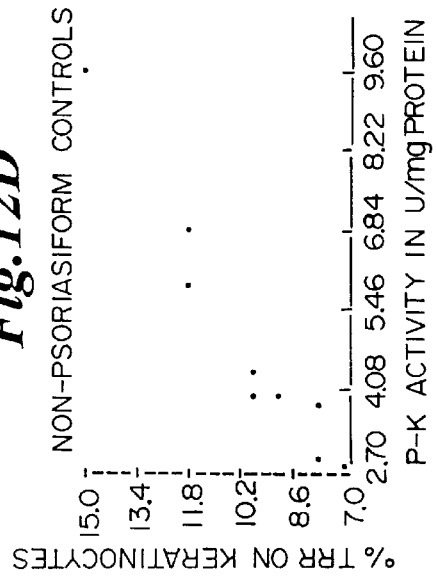
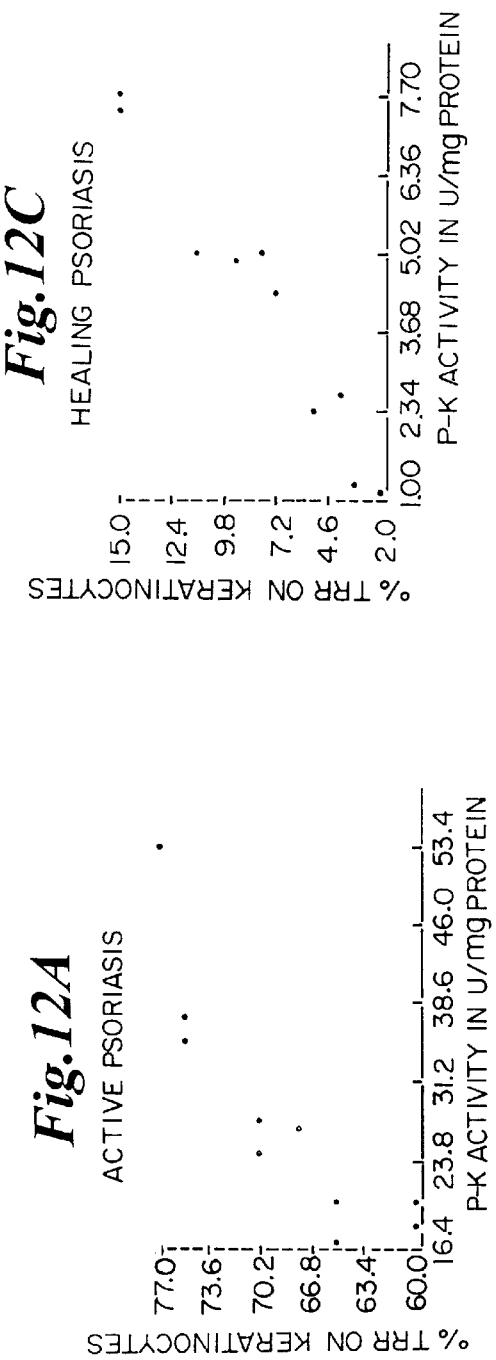
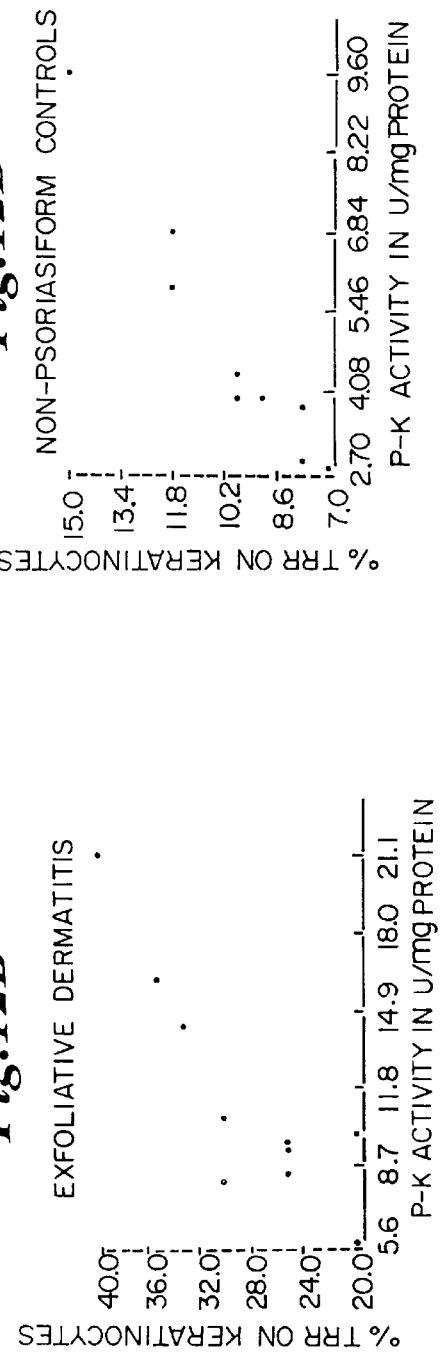

METHOD FOR TREATING PSORIASIS USING SELECTED PHOSPHORYLASE KINASE INHIBITOR AND ADDITIONAL COMPOUNDS

CROSS-REFERENCE

This application is a continuation-in-part of U.S. application Ser. No. 08/179,167 (now abandoned) by Madalene C. Y. Heng, filed Jan. 10, 1994, and also entitled "Combined Therapy for Psoriasis."

GOVERNMENT RIGHTS

The inventor of this invention is an employee of the Veterans Administration Medical Center in Sepulveda, California. The United States government, through the Veterans Administration, may have certain rights in this invention.

BACKGROUND OF THE INVENTION

This application is directed to a method for combined therapy of psoriasis based on methods for decreasing the increased activity of phosphorylase kinase in psoriasis.

Psoriasis is an inherited skin disease, the causal mechanisms of which are still unclear. However, the disease is believed to have a strong genetic basis. (H. Baker, "Psoriasis" in *Textbook of Dermatology* (A. Rook et al., eds., 4th ed., Blackwell Scientific Publications, Boston, 1986), vol. 2, pp. 1469–1532). In fact, this has been confirmed by recent findings from genetic studies of psoriatic families (G. Lomholt, "Psoriasis: Prevalence, Spontaneous Course, and Genetics" (Copenhagen, Denmark, GEC GAD, 1963); E. M. Farber et al., "Natural History of Psoriasis in 61 Twin Pairs," *Arch. Dermatol.* 109:207 (1974)), which suggest that at least two genes are implicated in the manifestation of psoriasis in predisposed individuals (J. T. Elder et al., "The Genetics of Psoriasis," *Arch. Dermatol.* 130:216–224 (1994)). One of these has been mapped to the short arm of the 6th chromosome (J. T. Elder et al. (1994), supra), and the other to the distal end of chromosome 17q (J. Tomfohrde et al., "Gene for Familial Psoriasis Susceptibility Mapped to the Distal End of Human Chromosome 17q," *Science* 264:1141–1145 (1994)). Chromosome 6 contain genes encoding not only class I and class II antigens of the major histocompatibility complex, but also class III (tumor necrosis factor-alpha [TNFα] molecules (J. T. Elder et al. (1994), supra). The expression of TNFα and its receptors has been shown to be enhanced in psoriatic skin (M. Kristensen et al., "Localization of Tumor Necrosis Factor-Alpha (TNFα) and Its Receptors in Normal and Psoriatic Skin: Epidermal Cells Express the 55 kD but not the 75 kD TNF Receptor," *Clin. Exp. Immun.* 94:354–362 (1993)), pointing to the possible role of superantigens in precipitating the disease (M. C. Y. Heng et al., "Erythroderma Associated with Mixed Lymphocyte-Endothelial Cell Interaction and Staphylococcal aureus Infection," *Br. J. Dermatol.* 115:693–705 (1986); B. J. Nickoloff et al., "Activated Keratinocytes Present Bacterial-Derived Superantigens to T Lymphocytes: Relevance to Psoriasis," *J. Dermatol. Sci.* 6:127–133 (1993)). Current investigations suggest that TNFα, through its capacity to influence the expression of the nuclear proto-oncoproteins, c-myc (J. X. Lin & J. Vilcek, "Tumor Necrosis Factor and Interleukin-1 Causes Rapid and Transient Stimulation of c-fos and c-myc mRNA in Fibroblasts," *J. Biol. Chem.* 262:11908–11911 (1987)) and c-fos (M. Hendriksson et al., "Phosphorylation Sites Mapping in the N-Terminal Domain of c-myc Modulate its Transforming Potential," *Oncogene* 8:3199–3209 (11993)), which are known to be important in regulation of cell growth and differentiation (O. Baadsgaard et al., "UM4D4+ (CDw60) T Cells Are Compartmentalized in Psoriatic Skin and Release Lymphokines that Induce a Keratinocyte Phenotype Expressed in Psoriatic Skin Lesions," *J. Invest. Dermatol.* 95:275–282 (1990)), may be important in increasing the gene expression of phosphorylase kinase. This hypothesis is consistent with current concepts involving the role of cytokines and proto-oncogenes in the phenotypic expression of psoriasis (J. T. Elder et al., "Protooncogene Expression in Normal and Psoriatic Skin," *J. Invest. Dermatol.* 94:19–25 (1990); G. Sozzi et al., "A t(10.17) Translocation Creates the RET/PTC2 Chimeric Transforming Sequence in Papillary Thyroid Carcinoma," *Genes, Chromosomes & Cancer* 9:244–250 (1994)).

It has been suggested that increased phosphorylase kinase activity may be due to defective regulation or presence of multiple copies of sequences encoding phosphorylase kinase in the genome of the psoriatic individual. This explanation is unlikely since, of the protein moieties under consideration, only the gene sequences encoding the regulatory subunit of cAMP-dependent protein kinase II has been mapped to the 17th chromosome (P. J. Barnard et al., "Mapping of the Phosphorylase Kinase Alpha Subunit Gene on the Mouse X Chromosome," *Cytogenet. & Cell Genet.* 53:91–94 (1990)). On the other hand, none of the phosphorylase kinase subunits have been mapped to chromosome 17. Instead, the alpha subunit of phosphorylase kinase has been mapped to the X chromosome, where it lies between the genes encoding the X-linked zinc finger protein and phosphoglycerate kinase genes (P. J. Williams et al., "Mapping of the Gene for X-Linked Liver Glycogenosis due to Phosphorylase Kinase Deficiency to Human Chromosome Region Xp22," *Genomics* 9:565–569 (1991); M. W. Kilimann, "Molecular Genetics of Phosphorylase Kinase: cDNA Cloning, Chromosomal Mapping and Isoform Structure," *J. Inher. Metab. Dis.* 13:435–441 (1990)); the β subunit to chromosome 16 (T. A. Jones et al., "Localization of the Gene Encoding the Catalytic Gamma Subunit of Phosphorylase Kinase to Human Chromosome Bands 7p12–q21," *Biochim. Biophys. Acta* 1048:24–29 (1990)), and the catalytic (γ) subunit to chromosome 7 (N. J. Lowe & H. B. Ridgeway, "Generalized Pustular Psoriasis Precipitated by Lithium," *N. Eng. J. Med.* 114:1788–1789 (1978)), and calmodulin (δ) subunit to chromosome 10. Aggravation of psoriasis by drugs which lower cAMP levels (M. C. Y. Heng & M. K. Heng, "Beta-Adrenoceptor Antagonist-Induced Psoriasiform Eruption," *Int. J. Dermatol.* 27:617–627 (1988); M. Sikorsia & J. F. Whitfield, "The Regulatory and Catalytic Subunits of Rat Liver Cyclic AMP-Dependent Protein Kinases Respond Differently to Thyroparathyroidectomy and 1α, 25-Dihydroxyvitamin D3," *Biochem. Biophys. Res. Commun.* 129:766–772 (1985)) also supports cAMP-dependent protein kinase deficiency and defective deactivation of phosphorylase kinase as a basic mechanism in psoriasiform hyperplasia in psoriasis.

That signal transduction molecules may be involved in triggering the active disease has been suggested by induction of the disease by trauma (E. M. Farber, "Role of Trauma in the Isomorphic Response in Psoriasis," *Arch. Dermatol.* 91:246–251 (1965); M. C. Y. Heng et al., "Electron Microscopic and Immunocytochemical Study of the Sequence of Events in Psoriatic Plaque Formation After Tape-Stripping," *Br. J. Dermatol.* 125:548–556 (1991)), as shown by previous reports of elevated levels of calmodulin (W. F. G. Tucker et al., "Biological Active Calmodulin Levels Are Elevated in Both Involved and Uninvolved Epidermis in Psoriasis," *J. Invest. Dermatol.* 82:298–299 (1984)), and of calmodulin-dependent enzymes such as phospholipase A2 (S. Forster et al., "Characterization and Activity of Phospholipase A2 in Normal Human Epidermis and in Lesion-Free Epidermis of Patients With Psoriasis and Eczema," *Br. J. Dermatol.* 112:135–147 (1985)), and by elevated prostaglandin $F_{2\alpha}$, ($PGF_{2\alpha}$), as well as other prostaglandins (C. L. Marcelo & J. J. Voorhees, "Cyclic Nucleotides and the Control of Psoriatic Cell Function," *Adv. Cyclic Nucleotide Res.* 12:1229–1237 (1980); S. Hammarstrom et al., "Increased Concentrations of Free Araclidonic Acid, Prostaglandins E2 and F2α, and of 12-Hydrcxy-5,8,10,14-Eicosatetraenoic Acid (HETE) in Epidermis of Psoriasis: Evidence for Perturbed Regulation of Arachidonic Acid Levels in Psoriasis," *Proc. Natl. Acad. Sci. USA* 72:5130–5134 (1975)). However, the reasons for reports of variable cAMP levels (G. G. Krueger, "Psoriasis: Current Concepts," in *Yearbook of Dermatology* (R. L. Dodson & B. H. Thiers, eds., Yearbook Medical Publishers, Inc., Chicago, 1981) pp. 13–70) and Decreased cAMP-Dependent Protein Kinase II Levels (D. E. Brion et al., "Deficiency of Cyclic AMP-Deperdent Protein Kinases in Human Psoriasis," *Proc. Natl. Acad. Sci. USA* 83:5272–5276 (1986)) are less clear.

The psoriatic plaque is characterized by hyperproliferative epidermal kinetics (E. J. Van Scott & T. M. Ekel, "Kinetics of Hyperplasia in Psoriasis," *Arch. Dermatol.* 88:373–381 (1963); R. Marks, "Epidermal Activity in the Involved and Uninvolved Skin of Patients with Psoriasis," *Br. J. Dermatol.* 98:399–404 (1978)), increased polyamine-dependent (N. J. Lowe, "Cutaneous Polyamines in Psoriasis," *Br. J. Dermatol.* 107:21–25 (1982)) cell cycling with an increased proliferative pool (G. D. Weinstein & J. L. McCollough, "Cytokinetics in Diseases of Epidermal Hyperplasia," *Annu. Rev. Med.* 24:345–352 (1973); S. Gelfant, "The Cell Cycle In Psoriasis," *Br. J. Dermatol.* 95:577 (1976); G. L. Grove, "Epidermal Cell Kinetics in Psoriasis," *Int. J. Dermatol.* 18:111–122 (1979)), followed by increased DNA synthesis (L. Rowe et al., "Mitoses in Normal and Psoriatic Epidermis," *Br. J. Dermatol.* 98:293–299 (1978)) and mitoses (J. G. Chafouleas et al., "Changes in Calmodulin and Its mRNA Accompany Reentry of Quiescent (GO) Cells Into the Cell Cycle," *Cell* 36:73–81 (1984)). Polyamine-induced cell cycling involves calcium-dependent (C. Cochet & E. M. Chamber, "Polyamine-Mediated Protein Phosphorylations: A Possible Target of Intracellular Polyamine Reactions," *Mol. Cell. Endocrinol.* 30:247–266 (1983)) protein phosphorylation (W. L. Combest, "Polyamines Differentially Inhibit Cyclic-AMP Dependent Protein Kinase-Mediated Phosphorylation in the Brain of a Tobacco Hornworm, Manduca sexta," *J. Neurochem.* 119:1581–1591 (1988)), and ATP generation, which is achieved not directly but through an unknown substrate (W. L. Combest, 1988, supra).

Cell cycling in psoriatic epidermis has been shown additionally to be modulated by epidermal growth factor (EGF) (J. T. Elder et al., "Overexpression of TGF-α in Psoriatic Epidermis," *Science* 243: 811–814 (1989); L. B. Nanney et al., "Altered $[^{125}I]$-Epidermal Growth Factor Binding and Receptor Distribution in Psoriasis," *J. Invest. Dermatol.*. 86: 260–266 (1986)).

Another hallmark of psoriasis is blood vessel abnormalities, which precede the development of overt histological psoriasis. High endothelial venules (HEVS) exist in psoriatic skin, and tannic acid staining material is present in the intercellular spaces between adjacent endothelial cells of the HEVs in psoriatic skin. The HEVs appear to be recognized by T8 (CD8) (cytotoxic/suppressor) lymphocytes, as the presence of HEVs was found to be related to the presence of T8 (CD8) lymphocytes in the epidermis. The tannic acid staining material may serve as a marker for HEVs recognized by the T8 (CD8) lymphocyte subset. The prior existence of HEVs in uninvolved psoriatic skin could account for the rapid egress of T8 (CD8) lymphocytes from the vasculature to the epidermis in response to trauma (M. C. Y. Heng et al., "High Endothelial Venules in Involved and Uninvolved Psoriatic Skin: Recognition by Homing Receptors on Cytotoxic T Lymphocytes," *Br. J. Dermatol.* 118: 315–326 (1988).

Psoriatic lesions can be induced by trauma in psoriatic individuals. Among the earliest changes noted in events leading to the formation of a psoriatic Flaque induced by tape-stripping was increased mobility of the epidermal Langerhans cells across the basement membrane, evidence of Langerhans cell-lymphocyte interaction, ard increased Langerhans cell activity or cytotoxicity. Collections of epidermal lymphocytes showing the features of blastoid transformation while in contact with processes from activated Langerhans cells suggest the involvement of Ia antigens in this process. These findings are consistent with an increased immune responsiveness to trauma, controlled by genes located at the HLA-D locus of the major histocompatibility complex, and mediated by enhanced cellular interactions (M. C. Y. Heng et al., "The Sequence of Events in Psoriatic Plaque Formation After Tape-Stripping," *Br. J. Dermatol.* 112: 517–532 (1985)).

There is some evidence that enhanced terminal differentiation of psoriatic keratinocytes, as shown by the increased expression of L-fucose specific binding sites on psoriatic keratinocytes (H. Roelfzema et al., "Studies on the Plasma Membrane of Normal and Psoriatic Keratinocytes. IV. Characterization of Glycoconjugates," *Br. J. Dermatol.* 105:509–516 (1981); M. C. Y. Heng et al., "Expression of the L-Fucose Moiety on Epidermal Keratinocytes in Psoriasis Induced by the Koebner Phenomenon," *Br. J. Dermatol.* 126:575–581 (1992); J. D. Zieski & I. A. Bernstein, "Modification of Cell Surface Glycoprotein: Addition of Fucosyl Residues During Epidermal Differentiation," *J. Cell. Biol.* 95:626–631 (1982)), may be equally important in the psoriatic process. Enhanced terminal differentiation has been shown to be an essential feature of the positive Koebner phenomenon, and L-fucose expression on epidermal keratinocytes is observed on keratinocytes undergoing terminal differentiation, such as in the Koebner phenomenon.

Biochemically, the process of terminal differentiation consists of a series of calcium-dependent reactions, all requiring energy and triggered by an influx of calcium into the keratinocyte (B. A. Dale et al., "Identification of Filaggrin in Cultured Mouse Keratinocytes and its Regulation by Calcium," *J. Invest. Dermatol.* 81:90s–95s (1983); H. Hennings et al., "Calcium Regulation of Growth and Differentiation of Mouse Epidermal Cells in Culture," *Cell* 19:245–254 (1980); S. T. Boyce & R. G. Ham, "Calcium Regulated Differentiation of Normal Human Keratinocytes in Chemically Defined Clonal Culture and Serum Free Serial Culture," *J. Invest. Dermatol.* 81:33s–40s (1983); C. K. Menon & P. M. Elias, "Ionic Calcium Reservoirs in Mammalian Epidermis: Ultrastructural Localization With Ion-Capture Cytochemistry," *J. Invest. Dermatol.* 84:508–512 (1985); P. Cohen, "The Role of cAMP-Dependent Protein Kinase in the Regulation of Glycogen Metabolism in Mammalian Skeletal Muscle," *Curr. Top. Cell. Regulat.* 14:117–196 (1978)).

Despite the increasing knowledge of the biochemical and genetic origins of psoriasis and the molecular events associated with the excess proliferation and terminal differentiation of epidermal cells that is the mark of the disease, effective treatments for psoriasis are still elusive. The disease is often subject to chronic and repeated remissions and exacerbations, which can be triggered by stress or exposure to environmental factors.

Because of the chronic nature of the disease and the necessity to continue treatment over long periods of time, new treatments of greater efficacy and lacking side effects are greatly desired. Preferably, such new treatments would be able to control the disease and prevent exacerbations caused by environmental factors, stress, and other factors that are not yet understood.

SUMMARY

An improved method of treatment and/or control of psoriasis is based on controlling: (1) the increased proliferation and (2) the enhanced terminal differentiation of psoriatic epidermis associated with the increased activity of epidermal phosphorylase kinase. Increased activity of phosphorylase kinase results in increased diversion of energy from glycogenolysis to calcium-dependent processes such as epidermal proliferation and terminal differentiation. By modulating the activity of this multisubunit enzyme at several points at once, the method of the present invention can better compensate for overproduction of the enzyme that might occur in psoriasis and provides more efficient control of its activity than does the use of only one drug having an effect on the activity of phosphorylase kinase.

In general, the method of the present invention is a method for preventing and/or inhibiting proliferation and terminal differentiation of psoriatic epidermal cells comprising the step of treating the psoriatic epidermal cells with a combination of substances affecting the activity of phosphorylase kinase. The combination of substances is selected from the group consisting of:

(1) a calmodulin inhibitor together with a stimulator of cAMP-dependent protein kinase II;

(2) a calmodulin inhibitor together with a calcium channel blocker;

(3) a stimulator of cAMP-dependent protein kinase II together with a calcium channel blocker; and (4) a calmodulin inhibitor together with a calcium channel blocker and a stimulator of cAMP-dependent protein kinase II.

Each of the substances is administered in a quantity sufficient to reduce the activity of phosphorylase kinase as measured by a phosphorylation of a suitable substrate.

The calmodulin inhibitor can be selected from the group consisting of cyclosporin A and anthralin. The cAMP-dependent protein kinase II can be selected from the group consisting of etretinate and Vitamin $D_3$ and derivatives thereof. The calcium channel blocker can be selected from the group consisting of diltiazem, isradipine, nifedipine, and verapamil.

Another aspect of the present invention is pharmaceutical compositions suitable for use in methods according to the present invention. These pharmaceutical compositions comprise:

(1) a combination of active agents selected from the group consisting of:

(a) a calmodulin inhibitor together with a stimulator of cAMP-dependent protein kinase II;

(b) a calmodulin inhibitor together with a calcium channel blocker;

(c) a stimulator of cAMP-dependent protein kinase II together with a calcium channel blocker; and (d) a calmodulin inhibitor together with a calcium channel blocker and a stimulator of cAMP-dependent protein kinase II; and (2) at least one pharmaceutically acceptable carrier.

Each of the active agents is present in the composition in a quantity sufficient to reduce the activity of phosphorylase kinase as measured by phosphorylation of a suitable substrate.

Typically, the calmodulin inhibitor is selected from the group consisting of zinc and cyclosporin A, the stimulator of cAMP-dependent protein kinase II is selected from the group consisting of etretinate and vitamin $D_3$ and derivatives thereof, and the calcium channel blocker is selected from the group consisting of diltiazem, isradipine, nifedipine, and verapamil.

Another aspect of the present invention is a method for preventing and/or inhibiting proliferation and terminal differentiation of psoriatic epidermal cells comprising the step of contacting the psoriatic epidermal cells with a selective phosphorylase kinase inhibitor in a quantity sufficient to reduce the activity of phosphorylase kinase as measured by phosphorylation of a suitable substrate. Typically, in this aspect, the selective phosphorylase kinase inhibitor is curcumin. The curcumin can be administered in a dose and by a route selected from oral administration from 250 mg to 2 g daily and a topical gel in the concentration of 0.1% to 10%.

Alternatively, the method can comprise the step of contacting the psoriatic epidermal cells with a selective phosphorylase kinase inhibitor together with one to four additional compounds, each compound being selected from the group consisting of:

(1) a compound selected from the group consisting of vitamin $D_3$ and a derivative thereof;

(2) etretinate;

(3) diltiazem; and (4) anthralin, the selective phosphorylase kinase inhibitor and the additional compounds each being administered in a quantity sufficient to reduce the activity of phosphorylase kinase as measured by phosphorylation of a suitable substrate.

Preferably, the selective phosphorylase kinase inhibitor is curcumin.

If the additional compound is vitamin $D_3$ or an analogue thereof, it is preferably $1\alpha,25$-dihydroxy vitamin $D_3$ in the form of an 0.005% ointment.

If the additional compound is etretinate, it is preferably administered in a dose of 25 mg from one to three times daily.

If the additional compound is anthralin, it is preferably administered in an ointment or paste in a concentration of from about 0.1% to about 3%.

If the additional compound is diltiazem, it is preferably administered at a dose of 60 mg three times daily.

BRIEF DESCRIPTION OF THE DRAWINGS

These and other features, aspects, and advantages of the present invention will become better understood with reference to the following description, appended claims, and the accompanying drawings where:

FIG. 12 shows the positive correlation of phosphorylase kinase activity with TRR expression on keratinocytes in (A) active psoriasis (r value 0.87); (B) exfoliative dermatitis (r value=0.88); (C) healing psoriasis (r value=0.98) and (D) non-psoriasiform dermatitis (eczemas and skin cancers; r value=0.96)

DESCRIPTION

I have developed a new method for treatment of psoriasis that utilizes the discovery that the activity of the enzyme phosphorylase kinase is increased in this disease. Although this enzyme (PK) is known to be abundant in muscles (E. G. Krebs, "Phosphorylation-Dephosphorylation of Enzymes," *Annu. Rev. Biochem.* 48:923–959 (1979); P. Cohen, "The Role of Protein Phosphorylation in Neural and Hormonal Control of Cellular Activity," *Nature* 296:613–620 (1982)), it has never previously been reported to be present in human epidermis.

Phosphorylase kinase, also known as ATP-phosphorylase b phosphotransferase (J. J. Davidson et al., "cDNA Cloning of a Liver Isoform of the Phosphoxylase Kinase α Subunit and Mapping of the Gene to Xp-22.2-p22.1, the Region of Human X-Linked Liver Glycogenolysis," *Proc. Natl. Acad. Sci. USA* 89:2096–2100 (1992)), integrates multiple signal transduction pathways and links them to the degradation of glycogen catalyzed by glycogen phosphorylase, thus generating ATP for subsequent metabolism. Specifically, phosphorylase kinase stimulates glycogenolysis by activating serine moieties in glycogen phosphorylase and by transferring the resulting ATP to convert phosphorylase b to phosphorylase a, which becomes available for phosphorylation-dephosphorylation reactions (J. J. Davidson et al. (1992), supra; P. Cohen (1978), supra; E. G. Krebs (1979), supra; P. Cohen (1982), supra). These ATP-dependent phosphorylation reactions mediated by phosphorylase kinase are: (a) triggered by calcium-calmodulin, because phosphorylase kinase is a calmodulin-containing enzyme; and (b) cAMP-dependent, because its activation status depends on cAMP-dependent protein kinases (J. J. Davidson et al. (1992), supra; P. Cohen (1978), supra; E. G. Krebs (1979), supra; P. Cohen (1982) supra)

In this way, the pathways signalled by injury, including physical injury, infections, and allergic reactions, are linked to ATP-dependent events of increased cell cycling (G. G. Krueger (1981), supra), increased cell division (G. G. Krueger (1981), supra), increased keratinocyte mobility, and increased terminal differentiation (M. C. Y. Heng et al., (1992), supra). These result in psoriasiform hyperproliferation, the clinical manifestation of psoriasis. It is believed that the increased phosphorylase kinase activity in psoriasis is due to increased synthesis of phosphorylase kinase due to the existence of multiple copies of the psoriatic gene in the genome of the psoriatic individual.

Phosphorylase kinase levels are linked to calmodulin levels and to calmodulin/cAMP ratios. These are then related to increased psoriatic activity.

Figure 1:
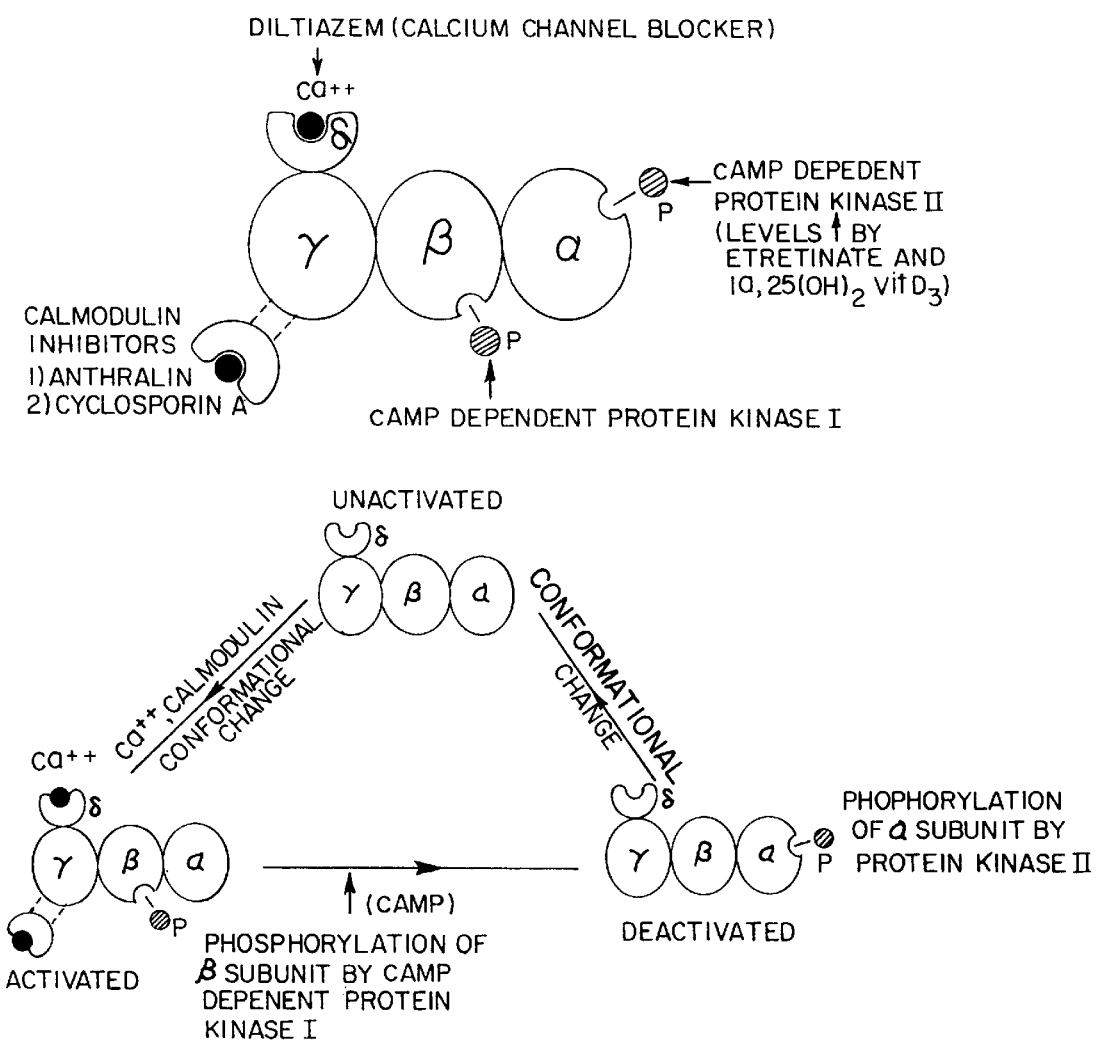
FIG. 1 is a diagram of the subunit structure of the enzyme phosphorylase kinase, showing the effects of various drugs on each subunit.

The enzyme phosphorylase kinase (PK) consists of four subunits, with a structure of $(\alpha\beta\gamma\Delta)_4$; the $\Delta$ subunit is calmodulin. The $\alpha$ and $\beta$ subunits are the regulatory subunits, with the $\gamma$ subunit being the catalytic subunit. The enzyme is activated by an influx of calcium ions into the cell from the extracellular fluid, whereupon binding of calcium ions to the calmodulin ($\Delta$) subunit results in a conformational change in the molecule, exposing the phosphate binding site on the $\beta$ subunit to be phosphorylated by cAMP-dependent protein kinase I, activating the enzyme. Activated phosphorylase kinase also associates reversibly with another molecule of calmodulin. As cAMP levels rise intracellularly, a second phosphate binding site on the $\alpha$ subunit is phosphorylated by cAMP-dependent protein kinase II, whereupon the molecule undergoes another conformational change, which deactivates the enzyme. Increased activity of phosphorylase kinase may therefore be due to increased influx of calcium ions into the cell, elevated levels of calmodulin, defective deactivation and/or elevated concentrations of the enzyme itself. These various relationships are shown in FIG. 1.

The activity of the skin isoform of phosphorylase kinase has been shown to be present in active psoriatic epidermis (M. C. Y. Heng et al., "Elevated Phosphorylase Kinase in Psoriatic Epidermis: Correlation with Increased Phosphorylation and Glycogenolysis," *Br. J. Dermatol.* 130:298–306 (1994)). This enzyme has recently been shown to have a wider substrate specificity than previously believed (C. J. Yuan et al., "Phosphorylase Kinase, a Metal Ion-Dependent Dual Specificity Kinase," *J. Biol. Chem.* 268:17683–17686 (1993)). Besides phosphorylating serine residues on glycogen phosphorylase and phosphorylase b in the presence of $Mg^{2+}$, phosphorylase kinase has been shown to have tyrosine kinase activity in the presence of $Mn^{2+}$ (C. J. Yuan et al. (1993), supra). In addition, phosphorylase kinase is able to phosphorylate threonine residues on troponin I (T. S. Huang et al., *FEBS Lett.* 42:249–252 (1974)) and even inositol in phosphatidylinositol (Z. Georgoussi & M. G. Heilmayer, Jr., *Biochemistry* 25:3867–3874 (1986)).

Phosphorylase kinase is thought to link ATP production through stimulation of glycogenolysis to phosphorylation-dephosphorylation processes in calcium-calmodulin triggered hormonal-dependent signaling pathways (J. J. Davidson (1992), supra). Although Applicant does not necessarily intend to be bound by this hypothesis, there is some evidence to support a hypothesis that phosphorylase kinase-mediated tyrosine kinase phosphorylation plays a role in the entry of non-cycling cells into the cell cycle. This evidence includes the following: (a) It is known that multiple phosphorylation of S6, a 40S ribosomal protein associated with the initiation of protein synthesis, is important for re-entry of non-cycling cells into the cell cycle (A. M. Gressner & I. G. Wool, "The Phosphorylation of Liver Ribosomal Proteins in Vivo," *J. Biol. Chem.* 249:6917–6925 (1974)). (b) Changes in calmodulin and its mRNA have been shown to accompany non-cycling (GO) cells into the early G1 phase of the cell cycle (J. G. Chafouleas et al. (1984), supra)). (c) The phosphorylation of S6 peptides has been shown to be modulated by EGF, and to involve signal transduction molecules such as cAMP (J. Martin-Perez et al., "EGF, PGF2 and Irsulin Induce the Phosphorylation of Identical S6 Peptides in Swiss Mouse 3T3 Cells: Effect of cAMP on Early Sites of Phosphorylation," *Cell* 36:287–294 (1984)). (d) EGF-dependent phosphorylation (J. J. Davidson et al. (1992), supra) has been shown to be triggered by calcium ions (E. J. O'Keefe & R. E. Payne, "Modulation of Epidermal Growth Factor-Receptor of Human Keratinocytes by Calcium Ion," *J. Invest Dermatol.* 81:231–235 (1983)).

To evaluate the role of phosphorylase kinase in cell cycling, the expression of transferrin receptors (TRR) on keratinocytes is used as a marker for cells capable of undergoing DNA synthesis, i.e., cycling cells (S. Eriksson et al., "Cell-Cycle Dependent Regulation of Mammalian Ribonucleotide Reductases. The S Phase Correlated Increase in Subunit M2 is Regulated by De Novo Protein Synthesis," *J. Biol. Chem.* 259:11695–11700 (1984); J. Laskey et al., "Evidence that Transferrin Supports Cell Proliferation by Supplying Iron for DNA Synthesis," *Exp. Cell. Res.* 176:87–95 (1988); L. M. Neckers & J. Cossman, "Transferrin Receptor Induction in Antigen-Stimulated Human T Lymphocytes Is Required for DNA Synthesis by Interleukin 2," *Proc. Natl. Acad. Sci. USA* 80:3494–3498 (1983)). The activity of phosphorylase kinase was then correlated with TRR expression in both psoriasiform dermatitic lesions (i.e., active psoriasis and exfoliative dermatitis) and non-psoriasiform lesions (i.e., healing psoriasis, eczemas, and skin cancers). Since calmodulin and cAMP levels modulate phosphorylase kinase activity, these molecules were also assayed (Example 6).

As indicated below (Example 6), increased activity of phosphorylase kinase was detected in both active psoriasis and exfoliative dermatitis, with parallel increases noted in calmodulin levels. In addition, increased phosphorylase kinase activity was observed to correlate with increased expression of transferrin receptors (TRR) on cycling keratinocytes, which reflects increase in size of the proliferative pool. Correlation of phosphorylase kinase activity with TRR expression in active psoriasis and exfoliative dermatitis, but not with healing psoriasis and non-psoriasiform lesions, indicates that increased activity of phosphorylase kinase is important for cell cycling and psoriasiform hyperplasia.

The role of calcium influx in inducing phosphorylase kinase activity is indicated by the fact that suppression of enzyme activity is induced by the administration of the calcium channel blocker, diltiazem, and the decreased phosphorylase kinase activity is associated with the healing phase of the disease. The findings of elevated levels of calmodulin in active and untreated psoriasis is consistent with its postulated role in psoriatic activity. The data discussed below shows a positive relationship between elevated levels of calmodulin and increased phosphorylase kinase activity in active and untreated psoriasis. These findings suggest that elevated calmodulin levels modulate phosphorylase kinase activity. Zinc has been shown to cause reciprocal changes in calmodulin and cAMP levels, which are in keeping with observations of inhibitory effects on calmodulin-stimulated protein kinase II on protein phosphorylation (R. P. Weinberger et al., "Effect of Zinc on Calmodulin-Stimulated Protein Kinase II and Protein Phosphorylation in Rat Cerebral Cortex," *J. Neurochem.* 57:605–614 (1991)).

In addition to increased activity of the enzyme resulting from an imbalance of activators as opposed to inhibitors of phosphorylase kinase, the increases activity of the enzyme may be due to increased concentrations of the enzyme. This can be due to either increased synthesis, i.e., increased mRNA production, or decreased degradation, i.e., an increased half-life of the enzyme. An increased mRNA production can be due to an increased expression of the phosphorylase kinase gene or to the presence of multiple copies of the phosphorylase kinase gene in the genome of psoriatic individuals. The phosphorylase kinase gene in psoriatic individuals may have increased susceptibility to induction by viral oncogenes or proto-oncogenes induced by cytokines, thus providing an explanation for the role of the lymphocyte-mediated immune response and the role of external antigens in psoriasis. This may account for the sensitivity of the disease to external environmental factors. The possibility that the psoriatic phosphorylase kinase gene may be inducible by cytokines, with the resulting epidermal proliferation modified by growth factors and their receptors is suggested by the association of psoriasis with T-cell-mediated responses, with resultant cytokine secretions such as IL-8, tumor necrosis factor, and interferon-$\gamma$. The resulting enhanced production of growth factors such as transforming growth factor-$\alpha$ and of its ligand, epidermal growth factor receptor, appears to be involved in the hyperproliferative manifestations of the disease.

Accordingly, an improved method of treatment of psoriasis utilizes the ability of phosphorylase kinase to be subject to more than one mode of activation and/or deactivation to produce a synergistic effect. Accordingly, such a method comprises the step of contacting the psoriatic epidermal cells with a combination of substances affecting the activity of phosphorylase kinase selected front the group consisting of:

(1) a calmodulin inhibitor together with a stimulator of cAMP-dependent protein kinase II;

(2) a calmodulin inhibitor together with a calcium channel blocker; and (3) a stimulator of cAMP-dependent protein kinase II together with a calcium channel blocker.

Each of the substances administered is administered in a quantity sufficient to reduce the activity of phosphorylase kinase as measured by phosphorylation of a suitable substrate. Typically, phosphorylase kinase activity is measured by determining the conversion rate of phosphorylase b to phosphorylase a, measuring radioactive phosphate transferred from [$^{32}$P]ATP to the phosphorylase b. Other assay methods are also known to the art.

As used herein, the term "combination" means that both of the substances are present in the psoriatic epidermal cells in sufficient concentrations at the same time. The substances, though, do not necessarily need to be administered at the same time or in a mixture; they can be administered in any convenient sequence and can be administered at different times or in different dosage forms.

Among suitable cAMP-dependent protein kinase II activators are the drugs etretinate and derivatives of Vitamin $D_3$ such as 1α,25-dihydroxy vitamin $D_3$.

Among suitable inhibitors of calmodulin are anthralin and cyclosporin A. Typically, anthralin is administered topically at concentrations of about 0.1% to about 2%. Another inhibitor of calmodulin activity is zinc (M. K. Heng et al., "Reciprocity Between Tissue Calmodulin and cAMP Levels: Modulation by Excess Zinc," *Br. J. Dermatol.* 129:280–285 (1993)). zinc can be administered orally or as a topical preparation, i.e., as an ointment.

Among calcium channel blockers are diltiazem, isradipine, nifedipine, and verapamil.

The dosages to be administered can be determined by one of ordinary skill in the art depending on the clinical severity of the disease, the age and weight of the patient, the exposure of the patient to conditions that may precipitate outbreaks of psoriasis, and other pharmacokinetic factors generally understood in the art, such as liver and kidney metabolism. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster, Dog, Monkey and Man," *Cancer Chemother. Rep.* 50: 219–244 (1966). Adjustments in the dosage regimen can be made to optimize the therapeutic response. Doses can be divided and administered on a daily basis or the dose can be reduced proportionally depending on the therapeutic situation.

Typically, these drugs will be administered orally, and they can be administered in conventional pill or liquid form. If administered in pill form, they can be administered in conventional formulations with excipients, fillers, preservatives, and other typical ingredients used in pharmaceutical formations in pill form. Typically, the drugs are administered in a conventional pharmaceutically acceptable formulation, typically including a carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The pharmaceutically acceptable formulation can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the substance for controlling the activity of phosphorylase kinase and other ingredients.

The drugs can also be administered in liquid form in conventional formulations, that can include preservatives, stabilizers, coloring, flavoring, and other generally accepted pharmaceutical ingredients. Typically, when the drugs are administered in liquid form, they will be in aqueous solution. The aqueous solution can contain buffers, and can contain alcohols such as ethyl alcohol or other pharmaceutically tolerated compounds.

Alternatively, the drugs can be administered by injection by one of several routes well known in the art. It is, however, generally preferred to administer the drugs orally.

The drugs can be administered from once per day to up to at least five times per day, depending on the severity of the disease, the total dosage to be administered, and the judgment of the treating physician. In some cases, the drugs need not be administered on a daily basis, but can be administered every other day, every third day, or on other such schedules. However, it is generally preferred to administer the drugs daily.

Another aspect of the present invention is the use of substances that block the synthesis or activity of Tumor Necrosis Factor-α (TNF-α) in conjunction with the other pharmacologically active agents in the treatment of psoriasis. TNF-α, a cytokine prominent in psoriasis (C. E. M. Griffiths, "Characterization of Intercellular Adhesion Molecule-1 and HLA-DR Antigen in Normal and Inflamed Skin: Modulation by Recombinant Gamma Interferon and Tumor Necrosis Factor," *J. Am. Acad. Dermatol.* 20:617–629 (1989)) is probably secreted by cytotoxic T lymphocytes and macrophages induced by trauma in the Koebner response (M. C. Y. Heng et al., High Endothelial Venules in Involved and Uninvolved Skin: Recognition by Homing Receptors on Cytotoxic T Lymphocytes," *Br. J. Dermatol.* 118:315–326 (1988); M. C. Y. Heng et al., "Electron and Immunocytochemical Studies of the Sequence of Events in Psoriatic Plaque Formation Following Tape-Stripping," *Br. J. Dermatol.* 125:548–556 (1991)).

TNF-α, a potent inducer of angiogenesis (M. Frater-Schroder et al., "Tumor Necrosis Factor-α, a Potent Inhibitor of Endothelial Cell Growth in Vitro, is Angiogenic in Vivo," *Proc. Natl. Acad. Sci. USA* 84:5277–5281 (1987); L. F. Fajardo et al., "Dual Role of Tumor Necrosis Factor-α in Angiogenesis," *Am. J. Pathol.* 140: 539–544 (1992); S. J. Liebovich et al., Macrophage-Induced Angiogenesis Is Mediated by Tumor Necrosis Factor-α," *Nature* 239:630–632 (1987)) and is the probable mediator of angiogenesis observed in psoriasis induced by the Koebner phenomenon (M. C. Y. Heng et al., "Expression of the L-fucose Moiety on Epidermal Keratinocytes in Psoriasis Induced by the Koebner Phenomenon: A. Sequential Study," *Br. J. Dermatol.* 126:575–581 (1992)).

Because TNF-α induces transcription reguLators (J. X. Lin et al., "Tumor Necrosis Factor and Interleukin-1 Cause Rapid and Transient Stimulation of c-fos and c-myc mRNA in Fibroblasts," *J. Biol. Chem.* 262: 11908–11911 (1997)), it may enhance the expression of the phosphorylase kinase gene. TNF-α also enhances the expression of epidermal growth factor receptors (K. Adachi et al., "Enhancement of Epidermal Growth Factor Expression on Glioma Cells by Recombinant TNF-α," *Cancer Immunol. Immunother.*) and their subsequent phosphorylation by tyrosine kinase (N. J. Donato et al., "Tumor Necrosis Factor Regulates Tyrosine Phosphorylation of A431 Carcinoma Cells," *Cell Growth Different.* 3:259–268 (1992), the presence of TNF-α may aggravate psoriasis.

Consequently, substances that block the synthesis of TNF-α, such as pentoxyfylline, and other anti-TNF-α substances, such as thalidomide, prednisone, or anti-TNF-α antibody, can be used in the treatment of psoriasis when used in combination with anti-phosphorylase kinase drugs. The substance that blocks the effect of TNF-α or inhibits the secretion of TNF-α is administered in a quantity sufficient to detectably reduce at least one of the consequences of TNF-α activity.

The same general considerations apply as to the use of pharmaceutical formulations, dosage, and route of administration as discussed above for anti-phosphorylase kinase drugs. A preferred dose for pentoxyfylline is about 5.7 mg per kg of body weight 3 times daily (400 mg).

Yet another aspect of the invention is the use of a selective phosphorylase kinase inhibitor for psoriasis therapy, alone or together with other agents. A particularly preferred selective phosphorylase kinase inhibitor is curcumin, administered in a quantity sufficient to reduce the activity of phosphorylase kinase as measured by phosphorylation of a suitable substrate. Typically, curcumin is administered orally in a dose of 250 mg to 2 g daily, or in a topical gel at 0.1% to 1 concentration. Curcumin can be administered alone, or, as described further below, in combination with other drugs such as vitamin $D_3$ or an analogue thereof, etretinate, diltiazem, or anthralin. Vitamin $D_3$ and its analogues are cAMP-dependent protein kinase II activators, as is etretinate. Anthralin is a calmodulin inhibitor. Diltiazem is a calcium-channel blocker.

Typically, a vitamin $D_3$ analogue such as 1α,25-dihydroxy vitamin $D_3$ is administered at a concentration of about 0.005% in the form of an ointment. An available ointment that is suitable is Donovex; it can be administered twice daily.

Curcumin (diferuloylmethane) is a major active component of the food flavor, turmeric (*Curcuma longa*; S. Reddy S & B. B. Aggarwal, "Curcumin Is a Non-Competitive and Selective Inhibitor of Phosphorylase Kinase," *FEBS Lett.* 341:19–22 (1994)). The anti-proliferative properties of curcumin in animals has been demonstrated by its inhibition of tumor initiation induced by benzo[a]pyrene and 7,12 dimethylbenz[a]anthracene (M. T. Huang et al., *Carcinogenesis* 13:2183–2186 (1992); M. A. Azuine & S. V. Bhide, *Nutr. Cancer* 17:77–83 (1992); M. A. Azuine & S. V. Bhide, *Int. J. Cancer* 51:412–415 (1992); M. Nagabhushan & S. V. Bhide, *J. Am. Coll. Nutr.* 11:192–198 (1992)), and inhibition of populations of various cell types (H. P. Ammon & M. A. Wahl, *Planta Med.* 57:1–7 (1991); R. R. Satoskar et al., *Int. J. Clin. Pharmacol. Res.* 24:651–654 (1986); T. N. B. Shankar et al., *Indian J. Exp. Biol.* 18:73–75 (1980); R. Srivastava, *Agents Action* 38:298–303 (1989); H. C. Huang et al., *Eur. J. Pharmacol.* 221:381–384 (1992)). In addition, curcumin inhibits the tumor promotion caused by phorbol esters (M. T. Huang et al., *Cancer Res.* 48:5941–5946 (1988); A. H. Conney et al., *Adv. Enzyme Regul.* 31: 385–396 (1991)). Recently, curcumin has been shown to inhibit pp60src (epidermal growth factor equivalent) tyrosine kinase via inhibition of phosphorylase kinase (S. Reddy & B. B. Aggarwal (1994), supra). It is possible that both the anti-tumor and anti-proliferative properties of curcumin may be mediated via its selective and non-competitive inhibition of phosphorylase kinase (S. Reddy & B. B. Aggarwal (1994), supra).

If curcumin is used alone as a therapy for psoriasis, it is preferably administered orally in a dose of from about 250 mg to about 2 g daily, or in a topical gel in a concentration of from about 0.1% to about 10%. Formulations for topical gels suitable for administration of curcumin are well known in the art; one suitable formulation uses an aloe vera gel base. Various stabilizers, excipients, and other conventional ingredients used in pharmaceutical gels can be used in the gel.

Alternatively, curcumin can be used together with one to four compounds, each compound being selected from the group consisting of:

(1) a compound selected from the group consisting of vitamin $D_3$ and a derivative thereof;
(2) etretinate;
(3) diltiazem; and
(4) anthralin.

The selective phosphorylase kinase inhibitor and the additional compounds each are administered in a quantity sufficient to reduce the activity of phosphorylase kinase as measured by phosphorylation of a suitable substrate.

Curcumin is administered as described above.

Typically, a vitamin $D_3$ analogue such as 1α,25-dihydroxy vitamin $D_3$ is administered at a concentration of about 0.005% in the form of an ointment. An available ointment that is suitable is Donovex; it can be administered twice daily.

Etretinate can be administered orally in a dose of 25 mg from once to three times daily.

Diltiazem can be administered orally in a dose of 60 mg three times daily.

Anthralin can be administered in the form of an ointment or paste at a concentration of from about 0.1% to about 3% once or more daily.

As described above, variations on these dosages and routes of administration can be determined by the treating physician depending on the severity of the disease, the response to therapy, and other underlying medical conditions that are present.

Yet another aspect of the present invention is pharmaceutical compositions for combined therapy. These pharmaceutical compositions contain any of the following combinations of active agents: (1) a calmodulin inhibitor together with a stimulator of cAMP-dependent protein kinase II; (2) a calmodulin inhibitor together with a calcium channel blocker; (3) a stimulator of cAMP-dependent protein kinase II together with a calcium channel blocker; and (4) a calmodulin inhibitor together with a calcium channel blocker and a stimulator of cAMP-dependent protein kinase II, together with at least one pharmaceutically acceptable carrier. Each of the active agents is present in the composition in a quantity sufficient to reduce the activity of phosphorylase kinase as measured by phosphorylation of a suitable substrate. These compositions are useful for administration of two or more of these agents at the same time by the same route. Typically, the route is oral.

If the pharmaceutical composition is to be administered orally, which is generally preferred, the calmodulin inhibitor is preferably zinc or cyclosporin A. The stimulator of cAMP-dependent protein kinase II is preferably etretinate or vitamin $D_3$ or derivatives thereof. The calcium channel blocker is preferably diltiazem, isradipine, nifedipine, or verapamil.

The dosage of each of the two or more pharmaceutically active agents in the combined pharmaceutical composition can be adjusted to meet clinical requirements and dosage ranges as described above.

A pharmaceutical composition for combined therapy according to the present invention can be in liquid or solid form, as discussed above for dosage forms for the individual therapeutic agents. If in solid form, it can be in pill, lozenge, or tablet form. Tablets can be prepared according to methods well known in the art, including tablets including a single layer containing both pharmaceutically active agents and tablets containing multiple layers, each one of the layers containing one of the pharmaceutically active agents, in this case one of two or three agents. The multiple layers can be separated by suitable excipients. Such compositions are well known in the art and need not be described further here.

Alternatively, a pharmaceutical composition for combined therapy according to the present invention can contain one or more of: (1) a calmodulin inhibitor; (2) a stimulator of cAMP-dependent protein kinase II; and (3) a calcium channel blocker together with a substance that blocks the effect of TNF-α or inhibits the secretion of TNF-α. Such a composition can be in the form of a multiply layered tablet as described above.

The invention is illustrated by the following Examples. These Examples are for illustrative purposes only and are not intended to limit the invention.

EXAMPLES

Example 1

Increased Phosphorylase Kinase Activity in Psoriatic Skin

Methods

Patients

Thirty subjects for the study were recruited from a dermatology clinic. They consisted of ten men with clinically active psoriasis who had not received any form of treatment for the disease (untreated/active group); ten men with resolving lesions of psoriasis after treatment with diltiazem 60 mg three times daily, with or without tar or methotrexate (treated/healing group); and ten men with the following untreated non-psoriatic skin diseases—3 eczema, 1 urticaria, 1 mycosis fungoides, 1 Darier's Disease, 1 melanoma, 1 tinea corporis and 2 squamous cell carcinoma (control group). Six punch biopsies, each 4 mm in diameter and weighing about 50 mg, were obtained from each patient, three from involved skin, and three from uninvolved skin. In psoriatic patients, "involved skin" refers to the active lesions from the active/untreated group, or resolving lesions from the healing/treated group. In the non-psoriatic control patients, and "involved skin" refers to the active untreated lesions of non-psoriatic skin disease. In each patient, biopsies from the uninvolved skin were taken at least 10 cm distance from those obtained from involved skin. Of the three biopsies obtained from each involved or uninvolved site, one was processed for microscopy as discussed below (Example 3) for determination of the density of glycogen granules and the other from biochemical assays.

Additional 4-mm punch biopsies were also taken from adjacent skin and divided longitudinally. One-half of each biopsy was fixed in 10% neutral buffered formalin and processed for light microscopy. Paraffin sections were stained with hematoxylin and eosin. Light microscopy was done to monitor the diagnosis of the specimen study. The other half was fixed in 2.5% glutaraldehyde, buffered to pH 7.3 with 0.1% sodium cacodylate, post-fixed in osmium tetroxide, treated en bloc with tannic acid, dehydrated in ethanol and propylene oxide, and embedded in a mixture of Epon 812 and Araldite 502. Silver sections (70–80 nm thick) were cut on a Sorvall MT2B ultramicrotome with a diamond knife (DuPont) and examined with a Phillips EM201 electron microscope. The glycogen content of the specimens was used to monitor the specimens, as described below.

For immunocytochemistry and lectin studies, adjacent skin was embedded in OCT compound (Tissue-Tek), snap-frozen in liquid nitrogen and stored at −70° C. until required. Serial cryostat sections (4 $\mu$m) were mounted on gelatin-coated slides and air-dried for 30 minutes at room temperature. The mounted sections were then freeze-dried for 4 hours, fixed in acetone for 20 minutes at room temperature, and air-dried for 5 minutes prior to immunostaining. Lectin binding assays using *Ulex europaeus* agglutinin I (UEA I) diluted to 1:200 were done to identify the terminally differentiated keratinocyte population to monitor the specimens.

Cytosolic Preparation of Epidermal Cells

Two skin biopsy samples, weighing approximately 100 mg, were used for biochemical analysis. The samples were stored at −70° C. until used. Each frozen sample, with the epidermal surface upward, was placed in a glass tube to which 3 ml Tris-HCl buffer (10 mM Tris-HCl, pH 7.8, 1 mM dithiothreitol (DTT), 3 mM $MgSO_4$ and 1 mM EGTA) was added, and homogenized vigorously with a teflon plunger in a Tris-R model K41 homogenizer for one second. Homogenization was repeated as necessary. The lysate of epidermal cells, separated from the dermis, was in the cytosolic solution. The fibroblasts which were inadvertently detached, together with a relatively intact piece of dermis, were removed by decanting the cytosolic solution into a 5-ml-capacity polypropylene test tube. The lysates were centrifuged at 3000×g for fifteen minutes. Membranes and other cytosolic organelles which formed a pellet at the bottom of the tube were removed. The supernatant, which contained the cytosolic component of epidermal cells, was then subjected to biochemical analysis.

A separate study, using biopsies from twelve subjects, was performed to validate the technique of separating the epidermis from the dermis in the skin samples. The samples, after thawing, were placed in a glass tube with the epidermis upwards, and suspended in Tris-HCl buffer solution containing 0.9% NaCl, for the separation of intact epidermal cells. The currents generated by stirring with the teflon plunger caused the separation of the epidermis from the dermis at the dermo-epidermal junction, which was confirmed by histological examination after the tissue samples, separated from the dermis by this procedure, were fixed in formalin and processed through paraffin sections through light microscopy. They consisted of 94.1±4.2% epidermal cells firom samples from psoriatic patients (n=6). These results showed the tissue from which the cytosolic preparation was obtained consisted mainly of epidermal cells.

Assay of Phosphorylase Kinase Concentration

Phosphorylase kinase activity was assayed by measuring the conversion rate of phosphorylase b or phosphorylase a, according to a modification of the method of Cohen (P. Cohen, "Phosphorylase Kinase From Rabbit Skeletal Muscle," *Meth. Enzvmol.* 99:243–250 (1983)). Briefly, phosphorylase kinase was assayed by measuring radioactive phosphate transferred from [$^{32}$P]ATP (DuPont, Wilmington, Del.) to the phosphorylase b, suspended in 30 mM cysteine solution, pH 7.0, in the process of conversion to the phosphorylase a form. Forty microliters of 30 mM cysteine solution., 50 $\mu$l of 0.25M β-glycerophosphate solution, 50 $\mu$l phosporylase b solution, and 20 $\mu$l of either PK standard solution or cytosolic samples were transferred to each 5-ml polypropylene test tube. The tubes were incubated at 30° C. for three to five minutes to equilibrate temperatures. At zero time, 40 μl [$^{32}$p]-ATP solution was added to each tube, mixed thoroughly, and incubated at 30° C. for 15 minutes. One ml of ice-cold 5% trichloroacetic acid (TCA) solution was then added to each tube. The tubes were then placed in ice, and cooled for 10 minutes or more. Each reaction mixture was then filtered through a filter paper with a pore size of 0.45 μm, and washed three times with 2 ml of cold 5% TCA solution. The filter paper containing phosphorylase b was counted in a liquid scintillation counter. Enzyme activity was determined based on a standard curve prepared with PK of known activity supplied by Sigma (St. Louis, Mo.).

The reproducibility of the methodology was assessed by duplicate measurements of unknown concentrations of the enzyme from randomly selected patients in the study population against known concentrations of PK. Firstly, 10 solutions of standard PK with known concentrations, ranging from 0 to 38 μg/mg protein, were assayed, and a linear standard graph was obtained. The average percent variation of each duplicate measurement from the mean was 4.70±4.24% (range 0–11.5%), and the linear correlation between the paired measurements was r=0.98. Secondly, enzyme activities from ten patients in the study population were measured twice for each skin sample. The corresponding reproducibility measurements for this assessment were 3.35±2.27% (range 0.27–8.81) and r=0.98.

Statistical Analysis

Comparison of the differences between mean measurements of the three patient groups was performed by multiple analysis of variance (MANOVA) and Tukey's, post hoc test. The results were considered statistically significant when $p<0.05$. All results are expressed as mean±SD.

Figure 2:
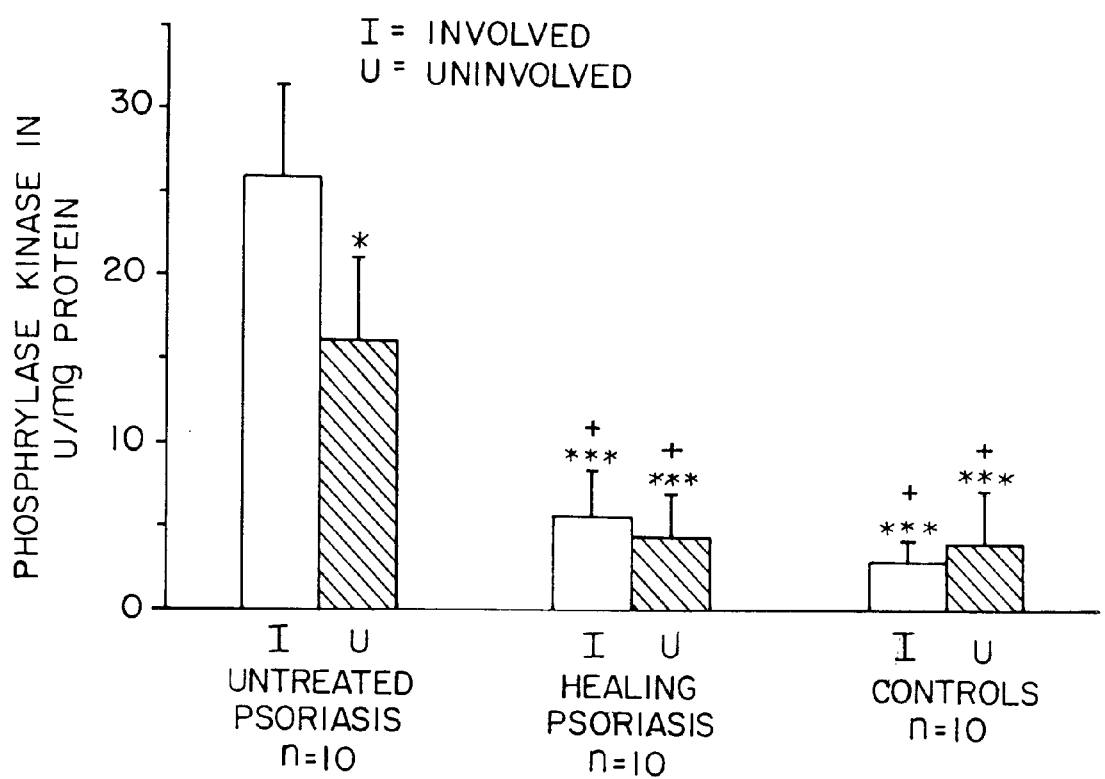
FIG. 2 is a graph showing the results of comparison of phosphorylase kinase activity in epidermal cells from patients with untreated psoriasis, patients with psoriasis undergoing treatment, and patients with non-psoriatic skin conditions.

The Results of Comparison of Phosphorylase Kinase Activity in the Cytosolic Supernatant of Epidermal Cells The results are shown in FIG. 2. The PK activity (U/mg protein) in the epidermis of the three groups of patients is shown in Table 1. In untreated psoriatic patients, the PK activity of the involved epidermis was significantly higher than in the uninvolved epidermis ($p<0.05$). The enzyme activity in both involved and uninvolved epidermis of untreated psoriatic patients was significantly higher than that of patients with treated psoriasis and non-psoriatic controls. The differences between PK levels of the involved epidermis in untreated psoriatics and both involved and uninvolved skin in the other two groups were all significant at the $p<0.001$ level; the corresponding differences for the uninvolved epidermis in untreated psoriatics were all significant at the $p<0.01$ level. The PK activities of the involved and uninvolved epidermis in the healing psoriatics and controls were all statistically similar.

TABLE 1

PHOSPHORYLASE KINASE ACTIVITY IN CYTOSOLIC SUPERNATANT OF EPIDERMAL CELLS

| Patient Status | Epidermis | Activity (U/mg Protein) |
|---|---|---|
| Active/Untreated | Involved | 25.9 ± 11.5 |
| Active/Untreated | Uninvolved | 16.2 ± 9.9 |
| Treated | Involved | 4.72 ± 2.95 |
| Treated | Uninvolved | 3.8 ± 1.95 |
| Control | Involved | 3.23 ± 1.55 |
| Control | Uninvolved | 4.41 ± 2.91 |

Example 2

Determination of Total Phosphorus in the Epidermal Cytosol

To each 5-ml-capacity glass test tube containing the test sample (1–10 μmol of phosphorus or 10–100 μl cytosolic sample), 40 μl of 2.0M perchloric acid solution was added, and boiled on a hot plate. Bumping was minimized by placing a capillary tube, sealed at the top, into the tube. One drop of potassium iodide solution (0.5 mg/ml) was added when the volume of each sample was reduced to about 30 μl. When the samples had evaporated almost to dryness, they were removed from the hot plate and cooled. Dilute ammonia solution (20 ml of 5.6M) was added to each sample, and the preparation heated again on a hot plate until it was dried. The sample was dissolved in exactly 1.0 ml distilled water when the test tube had cooled. Exactly 40 μl of ammonium molybdate reagent (2.0 mM $(NH_4)_6Mo_7O_{24} \cdot 4H_2O$ in 5.0M sulfuric acid solution) was added, followed by 10 μl of sodium sulfate solution (0.4M). Precisely ten minutes later, 20 μl stannous chloride working solution (20 mM $SnCl_2 \cdot 2H_2O$ in 0.5M HCl solution) was added. Thirty minutes later, the absorbance at 700 nm was read in a spectrophotometer. The reagent blank was subtracted from the absorbance reading of the sample. The concentration of inorganic ion in the sample was determined against standards of inorganic phosphate.

Inorganic phosphate concentration in each 1.0 ml of cytosolic sample was determined by adding molybdate reagent, followed by the addition of stannous chloride solution, and reading of the absorbance at 700 nm, without hydrolysis. The value of organic phosphorus was determined by subtracting the value of inorganic phosphate from the total phosphorous concentration.

Figure 3:
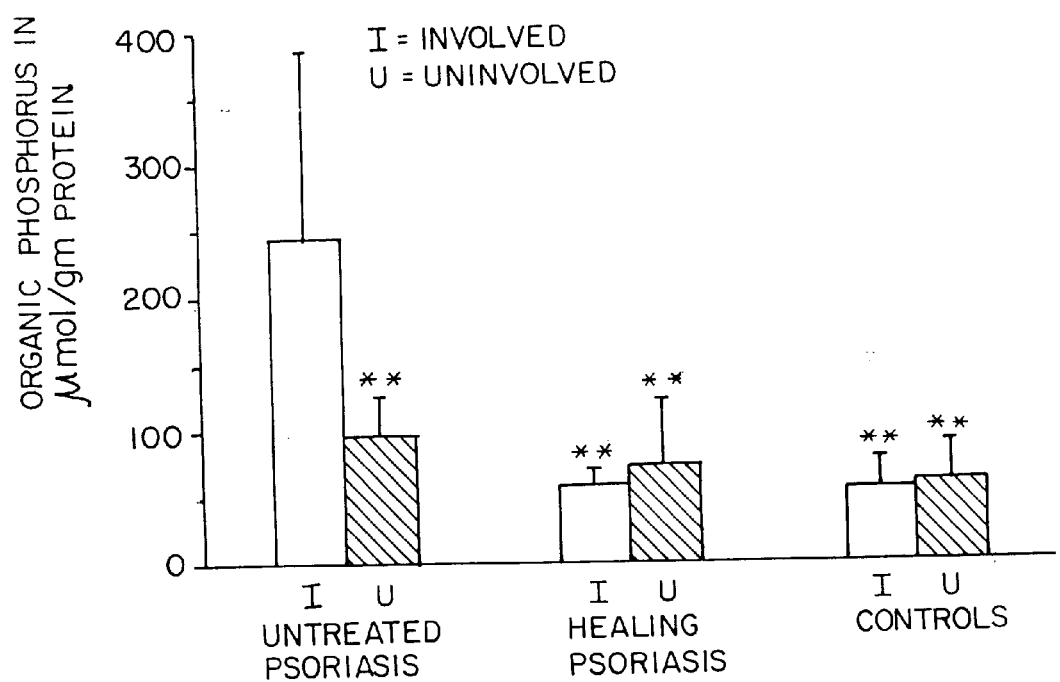
FIG. 3 is a graph showing the results of a comparison of organic phosphorus in epidermal cells from the same three groups of patients as in FIG. 2.
Figure 4:
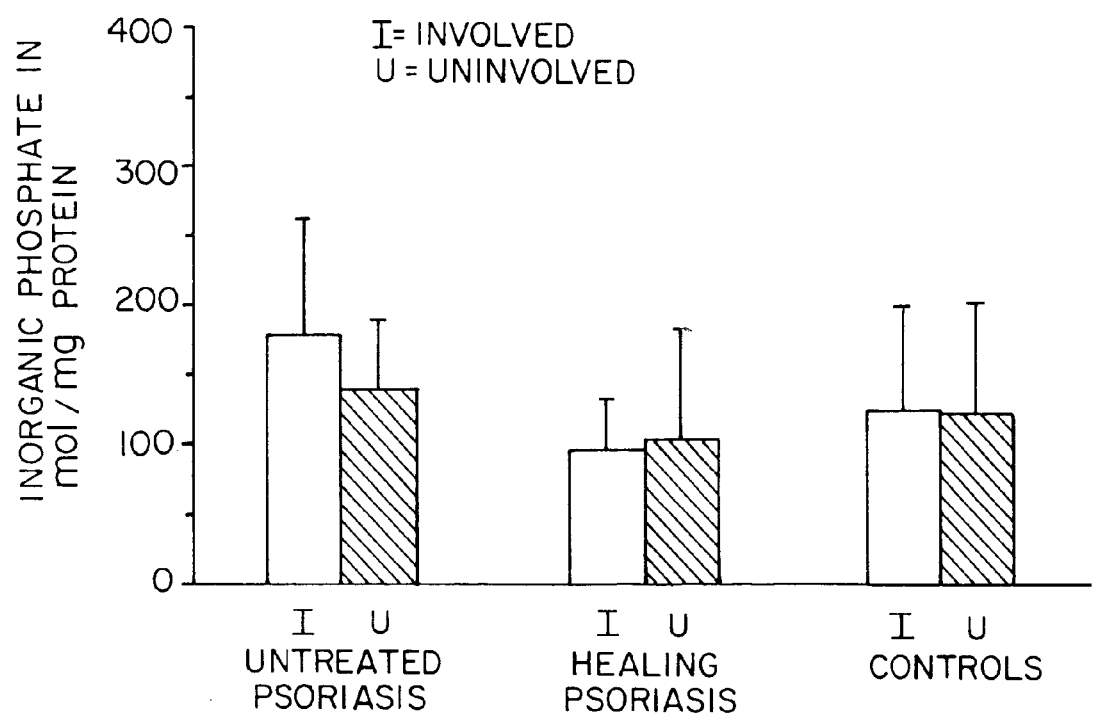
FIG. 4 is a graph showing the results of a comparison of inorganic phosphorus in epidermal cells from the same three groups of patients as in FIG. 2.

The results for organic phosphorus are shown in FIG. 3 and in Table 2; the results for inorganic phosphorus are shown in FIG. 4 and in Table 3. The levels in the involved and uninvolved skin in all three groups were statistically similar for inorganic phosphorus. For organic phosphorus, the concentration in the involved epidermis of the untreated psoriatics was significantly higher than the uninvolved skin of the same group, and the involved and uninvolved skin of the other two groups; the differences were all significant at the $p<0.005$ level. The values of the uninvolved skin in untreated psoriatics and the involved and uninvolved epidermis in the treated psoriasis group and controls were statistically similar.

TABLE 2

EPIDERMAL ORGANIC PHOSPHORUS CONCENTRATIONS

| Patient Status | Epidermis | Organic Phosphorus (μmol/g protein) |
|---|---|---|
| Active/Untreated | Involved | 244.3 ± 142.2 |
| Active/Untreated | Uninvolved | 96.9 ± 30.2 |
| Treated | Involved | 58.9 ± 12 |
| Treated | Uninvolved | 74.2 ± 49.1 |
| Control | Involved | 54.8 ± 23.6 |
| Control | Uninvolved | 58.7 ± 30.4 |

TABLE 3

EPIDERMAL INORGANIC PHOSPHORUS CONCENTRATIONS

| Patient Status | Epidermis | Inorganic Phosphate (μmol/g protein) |
|---|---|---|
| Active/Untreated | Involved | 178.3 ± 84.23 |
| Active/Untreated | Uninvolved | 139.44 ± 50.98 |
| Treated | Involved | 96.69 ± 36.24 |
| Treated | Uninvolved | 103.63 ± 79.91 |
| Control | Involved | 125.03 ± 74.95 |
| Control | Uninvolved | 121.43 ± 79.91 |

The levels of organic phosphorus were directly related to the levels of PK activity; the correlation coefficient between the two parameters was r=0.934 ($p<0.001$).

Example 3

Determination of the Density of Glycogen Granules

For each biopsy sample, the glycogen granules with within ten adjacent keratinocytes situated midway between the stratum corneum and the basal keratinocyte layer were photographed at a magnification of × 20,000, and printed at a further × 2.5 magnification on 203×254 mm Kodak paper (Eastman Kodak, Rochester, N.Y.), to a final magnification of × 50,000. The density of the glycogen granules was counted and determined for each square micron. Areas occupied by mitochondria, tonofilaments, and nuclei were eliminated from the count.

Figure 5A:
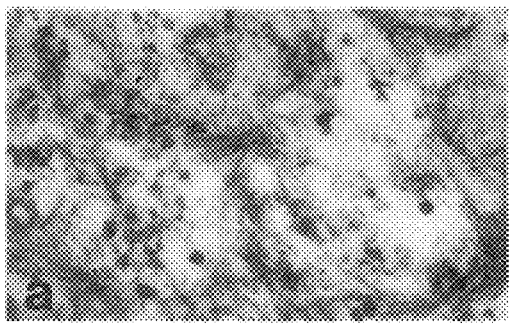
FIG. 5a is an electron photomicrograph of involved skin from untreated psoriatic patients, showing glycogen granules.
Figure 5B:
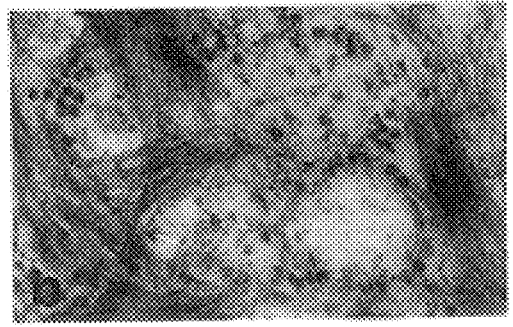
FIG. 5b is an electron photomicrograph of uninvolved skin from untreated psoriatic patients, showing glycogen granules.
Figure 5C:
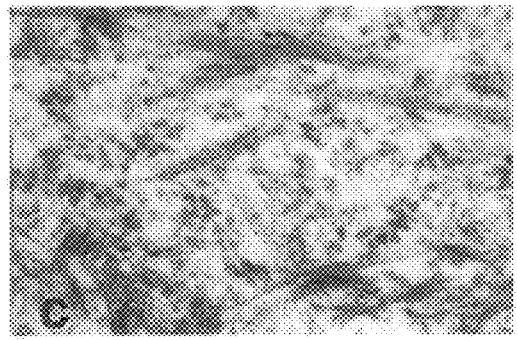
FIG. 5c is an electron photomicrograph of involved skin from treated psoriatic patients, showing glycogen granules.
Figure 5D:
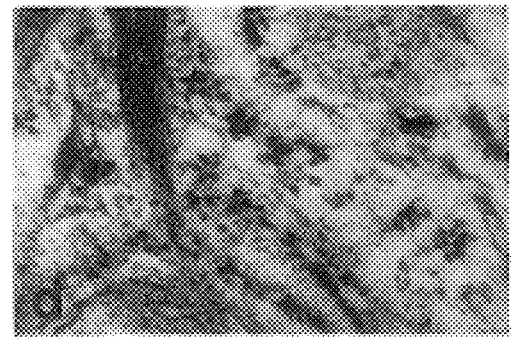
FIG. 5d is an electron photomicrograph of uninvolved skin from treated psoriatic patients, showing glycogen granules.
Figure 5E:
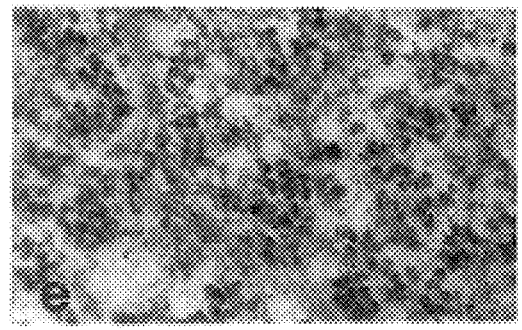
FIG. 5e is an electron photomicrograph of involved skin from patients with non-psoriatic skin disorders, showing glycogen granules.
Figure 5F:
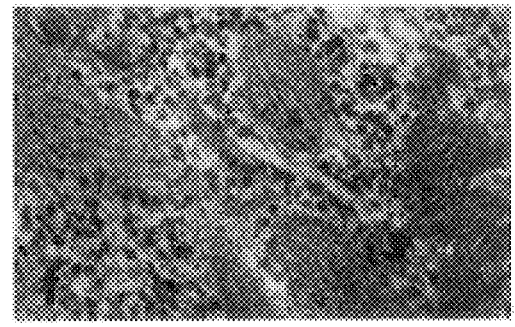
FIG. 5f is an electron photomicrograph of uninvolved skin from patients with non-psoriatic skin disorders, showing glycogen granules.

The results are shown in Table 4. Electron microscopic examination of the skin specimens showed a paucity of glycogen granules in both involved (FIG. 5a) and uninvolved (FIG. 5b) skin of untreated psoriasis, intermediate values in involved (FIG. 5c) and uninvolved (FIG. 5d) epidermis of treated psoriasis, and abundant glycogen granules both in involved (FIG. 5e) and uninvolved (FIG. 5f) epidermis of non-psoriatic controls.

TABLE 4

DENSITY OF EPIDERMAL GLYCOGEN GRANULES

| Patient Status | Epidermis | Density of Glycogen Granules (granules/$\mu m^2$) |
|---|---|---|
| Active/Untreated | Involved | 101 ± 2.8 |
| Active/Untreated | Uninvolved | 20.5 ± 4.3 |
| Treated | Involved | 28.5 ± 5.2 |
| Treated | Uninvolved | 33.6 ± 6.5 |
| Control | Involved | 60.3 ± 15.7 |
| Control | Uninvolved | 82.0 ± 14.8 |

The glycogen density in the involved skin of untreated psoriasis was significantly lower than the uninvolved skin of the same group of patients (p<0.05) and both involved and uninvolved skin of patients with treated psoriasis (p<0.01) and controls (p<0.001). In he treated and control groups, there was no significant difference between the density of glycogen granules in involved and uninvolved skin biopsies. However, the density in the treated psoriatics was significantly lower than the controls (p<0.01).

The density of glycogen granules is inversely related to glycogenolytic activity, so that increased glycogenolysis results in a lower density of glycogen is granules. Accordingly, these findings are consistent with increased glycogenolysis in both involved and uninvolved active psoriatic skin, but not in involved and uninvolved non-psoriatic biopsies.

Example 4

Determination of cAMP Concentration

Figure 6:
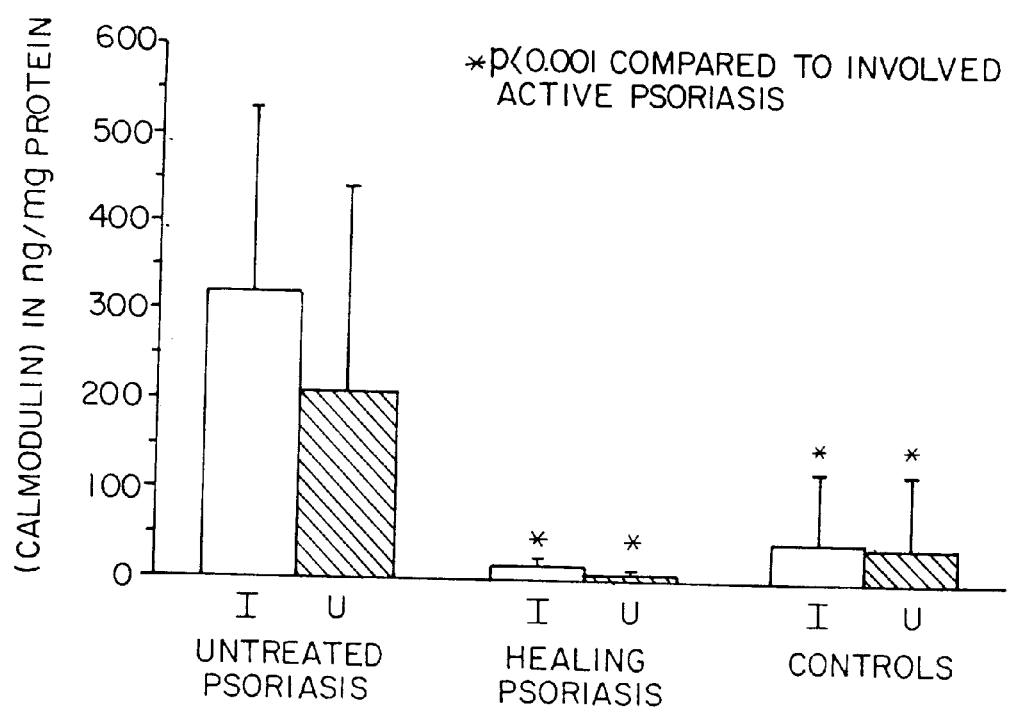
FIG. 6 is a graph showing the results of a comparison of cAMP levels in epidermal cells from the same three groups of patients as in FIG. 2.

To determine cAMP concentration in the cytosol samples as prepared as described above, exactly 300 $\mu$l of cytosolic solution was mixed with an equal volume of 10% trichloroacetic acid (TCA). The mixture was then centrifuged at 10,000×g at 4° C. for 15 minutes. The supernatant from the centrifugation was then extracted with five volumes of ethyl ether four times. The liquid phase with some ether was further evaporated in a vacuum until no smell of ether could be detected. The volume of aqueous solution containing cAMP was further measured. Exactly 100 $\mu$l of the aqueous solution was then subjected to radioimmunoassay using the DuPont cAMP radioimmunoassay kit (DuPont, Wilmington, Del.). Values for all samples were determined by duplicate measurements. The results are shown in Table 5 and in FIG. 6. None of the comparisons achieved levels of statistical significance.

TABLE 5 cAMP LEVELS IN EPIDERMAL CYTOSOL SAMPLES

| Patient Status | Epidermis | cAMP Level ($\mu$mol/mg Protein) |
|---|---|---|
| Active/Untreated | Involved | 13.5 ± 8.1 |
| Active/Untreated | Uninvolved | 20.9 ± 12.6 |
| Treated | Involved | 18.5 ± 11.0 |
| Treated | Uninvolved | 18.8 ± 11.3 |
| Control | Involved | 19.3 ± 105 |
| Control | Uninvolved | 19.4 ± 11.1 |

Example 5

Determination of Calmodulin Concentration and Calmodulin/cAMP Ratio

Calmodulin concentrations in the cytosol of human epidermal cells suspended in Tris-buffer solution prepared as described above were determined by the radioimmunoassay method using the RIA kit supplied by DuPont Co. In this procedure, 100 $\mu$l cytosolic solution was mixed with 100 $\mu$l of iodinated calmodulin solution and 100 $\mu$l of anti-serum complex. After 16 to 20 hours of incubation at 4° C., 0.5 ml of the second antibody solution was added and mixed thoroughly. The mixtures were centrifuged at 7,000×g for 15 minutes and the radioactivities of the precipitates were determined by liquid scintillation counting. These radioactivities were then converted to ng calmodulin/mg protein by plotting against the standard solution of calmodulin. All values were determined in duplicate. The calmodulin concentrations were then used to calculate calmodulin/cAMP ratios.

Figure 7:
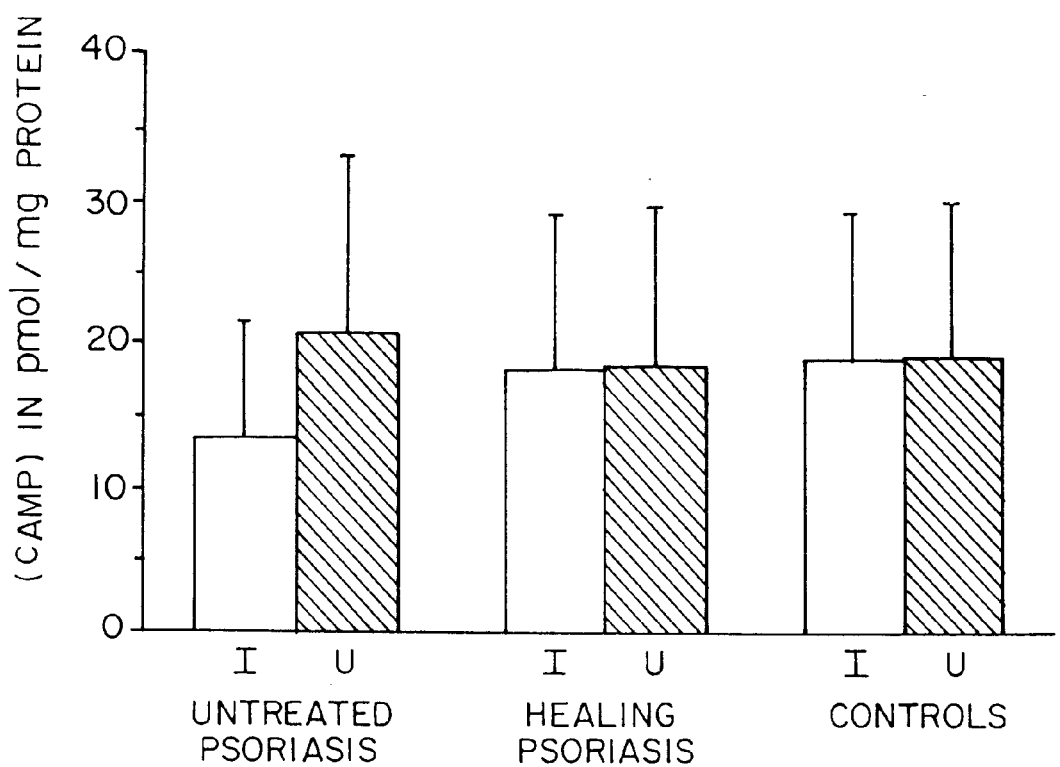
FIG. 7 is a graph showing the results of a comparison of calmodulin levels in epidermal cells from the same three groups of patients as in FIG. 2.
Figure 8:
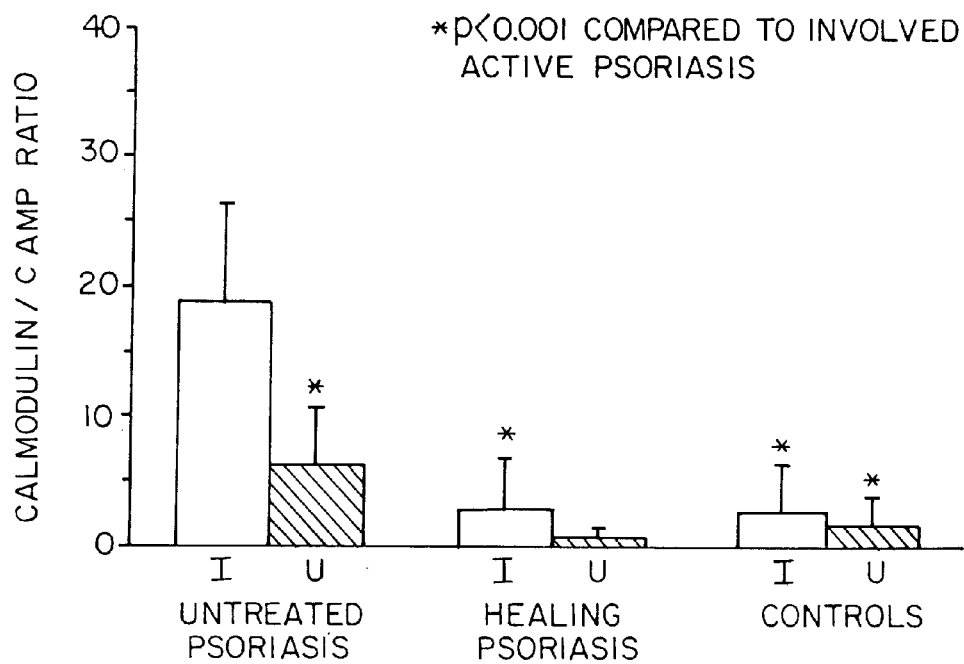
FIG. 8 is a graph showing the results of a comparison of calmodulin/cAMP ratios in epidermal cells from the same three groups of patients as in FIG. 2.
Figure 9:
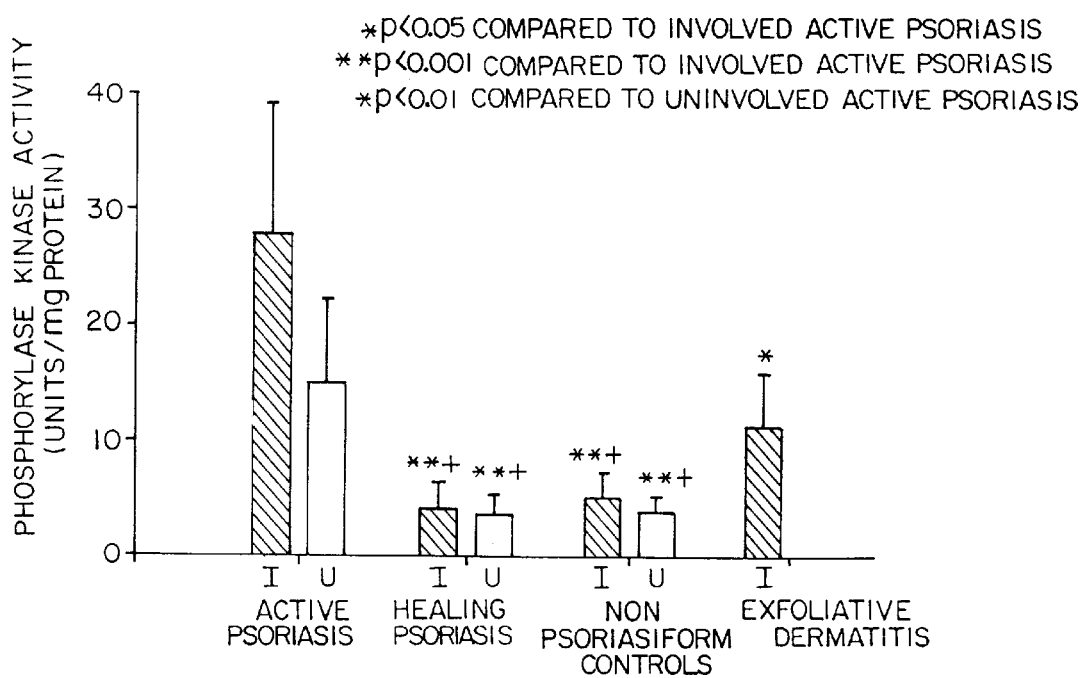
FIG. 9 is a graph showing phosphorylase kinase activity in units/mg protein for another group of patients, comparing patients with active psoriasis, patients with healing psoriasis, non-psoriasiform controls, and patients with exfoliative dermatitis (n=10 for each group); data is shown as mean±SD.
Figure 10:
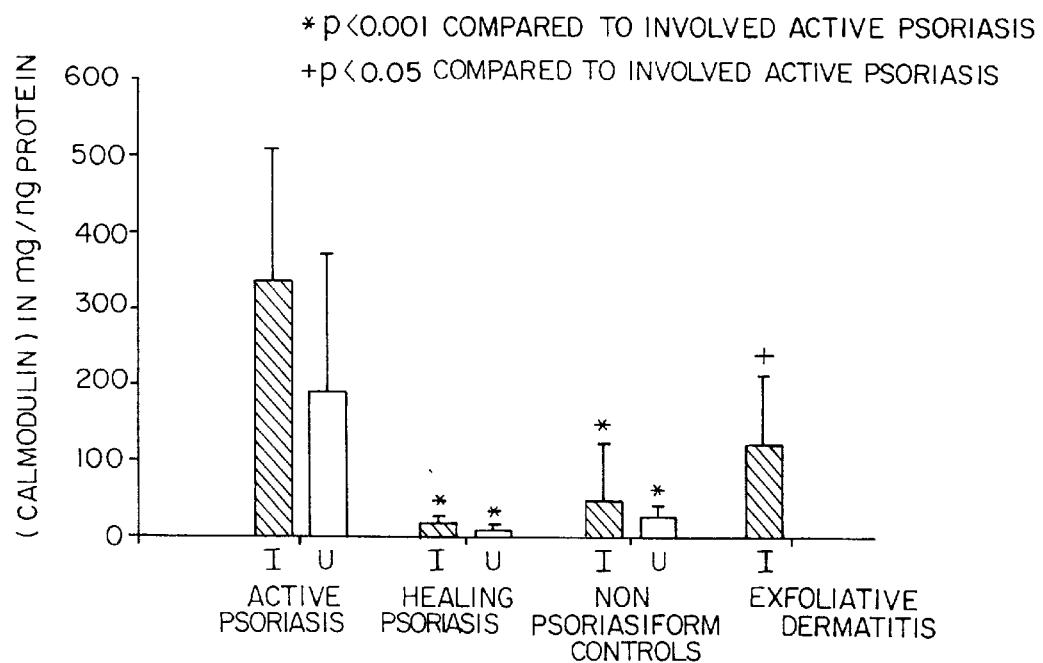
FIG. 10 is a graph showing calmodulin concentration in ng/mg protein for the same groups of patients as in FIG. 9; calmodulin levels, expressed as ng/mg protein, are measured by RIA against known standards, in cytosolic epidermal preparations from involved (hatched bars) and uninvolved (open bars) skin of active psoriasis (n=10), healing psoriasis (n=10), and non-psoriasiform (eczemas (n=4) and skin cancers (n=6)) and exfoliative dermatitic controls.

The results are shown in Table 6 and FIG. 7 for the calmodulin concentrations and in Table 7 and FIG. 8 for the calmodulin/cAMP. Calmodulin/cAMP ratios from involved skin of active/untreated psoriasis were highly significantly elevated (p<0.001) compared to all other groups. No other comparisons achieved levels of significance.

TABLE 6

CALMODULIN LEVELS IN EPIDERMAL CYTOSOL SAMPLES

| Patient Status | Epidermis | Calmodulin Level (ng/mg protein) |
|---|---|---|
| Active/Untreated | Involved | 321 ± 211 |
| Active/Untreated | Uninvolved | 210 ± 223 |
| Treated | Involved | 18.1 ± 9.5 |
| Treated | Uninvolved | 9.1 ± 5.5 |
| Control | Involved | 46.2 ± 79.3 |
| Control | Uninvolved | 42.1 ± 81.8 |

TABLE 7

CALMODULIN/CAMP RATIOS IN EPIDERMAL CYTOSOL SAMPLES

| Patient Status | Epidermis | Calmodulin/cAMP Ratio |
|---|---|---|
| Active/Untreated | Involved | 18.9 ± 7.4 |
| Active/Untreated | Uninvolved | 6.2 ± 4.6 |
| Treated | Involved | 2.9 ± 4.1 |
| Treated | Uninvolved | 0.77 ± 0.7 |
| Control | Involved | 2.7 ± 3.7 |
| Control | Uninvolved | 1.68 ± 2.2 |

Example 6

Increased Activity of Phosphorylase Kinase and Exfoliative Dermatitis: Correlation with Calmodulin Levels, Proliferative Pool and Disease Activity As a confirmation of the results in Examples 1 and 5 and a test of the model correlating increased activity of phosphorylase kinase with psoriasiform pathology, further studies were performed on patients with exfoliative dermatitis as well as psoriasis. This Example is designed to correlate phosphorylase kinase activity with the pool of cycling cells in psoriasis.

Methods

Patient Population. The subjects for the study were recruited from the Dermatology Clinics at the Veterans Administration Medical Center, Sepulveda, Calif. These consisted of 10 men with clinically active untreated psoriasis, characterized by marked parakeratosis on histopathology (untreated/active group); 10 men with healing lesions of psoriasis after therapy with diltiazem 60 mg t.i.d. (27) in 8 patients, together with 0.005% Dovonex (Vitamin $D_3$ analogue) ointment in 4 patients and 1% hydrocortisone ointment in 6 patients, and either dicloxacillin (500 mg q.i.d.) or cephradine (500 mg q.i.d.) directed against culture-positive *Staphylococcus aureus* in 9 patients and oral penicillin (pen VK 500 mg q.i.d.) against culture positive Streptococcus sp. in 1 patient (treated/healing 4 group, characterized by acanthosis without parakeratosis); and 4 men with eczemas and 6 men with skin cancers (3 with squamous cell carcinomas and 3 with basal cell carcinomas) serving as non-psoriasiform proliferative controls. Involved skin from 10 patients with exfoliative dermatitis associated with culture positive *Staphylococcus aureus* from the skin was also studied (M. C. Y. Heng et al. (1986), supra). These were characterized by marked epidermal hyperplasia with parakeratosis (psoriasiform hyperplasia) on histopathology. Three punch biopsies, each 4 mm in diameter and weighing about 100 mg, were obtained from each site (involved and uninvolved skin), and processed for histology, immunocytochemical studies and biochemical analysis. In psoriatic patients, involved skin refers to the active lesions from the active/untreated group, or healing lesions from the healing/treated group. Informed consent for the biopsies was approved by the Human Subjects Subcommittee of Sepulveda VA Medical Center, California, and obtained from all patients.

Assay of Phosphorylase Kinase Activity. The serine kinase activity of phosphorylase kinase was determined by measuring the incorporation of $^{32}p$ transferred from $[^{32}P]$ ATP to phosphorylase b as detailed above in Example 1.

Assay of cAMP Concentration. Exactly 300 µl of cytosolic solution was mixed with an equal volume of 10% TCA (trichloracetic acid). The mixture was then centrifuged at 10,000×g at 4° C. for 15 mins. The supernatant was then extracted with 5 volumes of ethyl ether four times. The liquid phase with some ether was further evaporated in a vacuum until no smell of ether could be detected. The volume of aqueous solution containing cAMP was further measured. Exactly 100 µl of the aqueous solution was then subjected to radioimrnunoassay using the Dupont cAMP Radioimmunoassay Kit. All the values of the samples were determined by duplicate measurements.

Assay of Calmodulin Concentration. Calmodulin concentrations in the cytosol of human epidermal cells suspended in Tris buffer solution) 10 mM Tris-HCl, pH 7.8 containing 1 mM dithioethreitol, 3 mM MgSO4 and 1 mM EGTA) were determined by the radioimmunoassay method using the RIA kit supplied by Dupont Co. In this procedure, 100 µl cytosolic solution was mixed with 100 µl of iodinated calmodulin solution and 100 µl of antiserum complex. After 16–20 hours of incubation at 4° C., 0.5 ml of the second antibody solution was added and mixed thoroughly. The mixtures were centrifuged at 7,000×g for 15 mins and the radioactivities of precipitates were determined by a Beckman liquid scintillation counter. These activities were converted to ng calmodulin/mg protein by plotting against a standard solution of calmodulin. All the values of the samples were determined by duplicate measurements.

Assessment of Transferrin Receptors (TRR) Expression on Keratinocytes. The expression of TRR on basal and suprabasal keratinocytes (FIG. 11) was quantified as the percentage of TRR+ keratinocytes per rete ridge. The keratinocytes of 10 consecutive rete ridges were assessed in this way for each biopsy and the results averaged.

Results.

The results have been summarized in FIGS. 9–12.

Comparison of Phosphorylase Kinase Activity in Cytosolic Supernatant of Epidermal Cells. To evaluate the significance of phosphorylase kinase activity in psoriatic activity, phosphorylase kinase activity was determined in involved and uninvolved skin samples from active/untreated psoriasis with markedly parakeratotic epidermis, and healing/treated psoriasis without parakeratosis. To distinguish between psoriasiform hyperplasia and non-psoriasiform hyperplasia, skin biopsy specimens with marked parakeratosis from active psoriasis and exfoliative dermatitis were studied as examples of psoriasiform hyperolasia and specimens without parakeratosis from healing psoriasis, eczemas and skin cancers as examples of non-psoriasiform hyperplasia. The phosphorylase kinase activity (units per mg protein) in the epidermal cytosolic supernatant of the 4 groups (FIG. 9) were—active psoriasis: involved epidermis 27.9±11.4 (SD), uninvolved epidermis 15.1±7.2 (SD); healing psoriasis: involved epidermis 4.1±2.4, uninvolved epidermis 3.6±1.8; non psoriasiform (skin cancer and eczemas) controls: involved epidermis 5.1±2.2, uninvolved epidermis 3.8±1.4; and exfoliative dermatitis: involved epidermis 11.3±4.6. In active psoriatic patients, the phosphorylase kinase activity of the involved epidermis was significantly higher than involved and uninvolved skin of healing psoriasis ($p<0.001$) and non-psoriasiform controls ($p<0.001$); marginally higher when compared to exfoliative dermatitis ($p<0.05$), but not significantly different from uninvolved skin of active psoriasis. Phosphorylase kinase activity of uninvolved skin of active psoriasis was also significantly higher ($p<0.01$) than involved and uninvolved skin of healing psoriasis and non-psoriasiform skin cancer controls. The phosphorylase kinase activity of the involved and uninvolved epidermis in the healing psoriatics and non-psoriasiform controls were all statistically similar.

Comparison of Calmodulin Levels in Cytosolic Supernatant from Epidermal Cells. Calmodulin levels in the above samples were also determined since phosphorylase kinase is a calmodulin-containing enzyme. In addition, calmodulin levels are important in determining the activation status of phosphorylase kinase since the activated molecule binds to an additional molecule of calmodulin. The calmodulin levels (FIG. 10) in ng/mg protein of the 4 groups of patients were—active psoriasis: involved epidermis 338±172 (SD), uninvolved epidermis 192±183; healing psoriasis: involved epidermis 18.1±9.5, uninvolved skin 9.1±5.5; non-psoriasiform controls: involved skin 48.1±75.3, uninvolved skin 27.5±14.6; and exfoliative dermatitis: involved skin 122.6±91.8. The calmodulin levels in involved skin of active psoriasis were significantly higher than involved and uninvolved skin from both healing psoriasis ($p<0.001$) and non-psoriasiform controls ($p<0.001$). The calmodulin levels in active psoriasis were only marginally higher ($p<0.05$) than exfoliative dermatitis. Calmodulin levels in exfoliative dermatitis were significantly different ($p<0.01$) from both involved and uninvolved skin of healing/treated psoriasis and uninvolved skin of non-psoriasiform controls, but not significantly different from uninvolved skin of active psoriasis. No other comparisons achieved levels of significance.

Figure 11A:
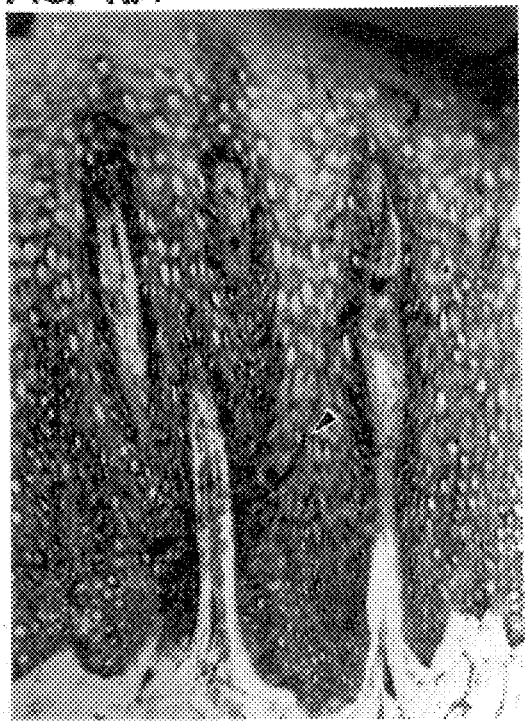
FIG. 11 shows photomicrographs depicting transferrin receptor (TRR) expression (single arrows) on epidermal keratinocytes demonstrated by anti-TRR monoclonal antibodies (Becton-Dickinson; diluted 1:10) in (a) active psoriasis; (b) exfoliative dermatitis; (c) healing psoriasis; and (d) eczema (poison oak) (×250)
Figure 11B:
Figure 11C:
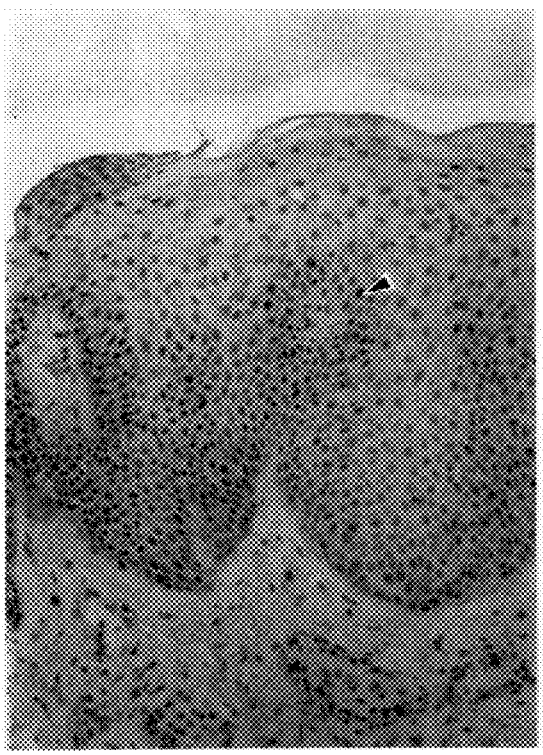
Figure 11D:
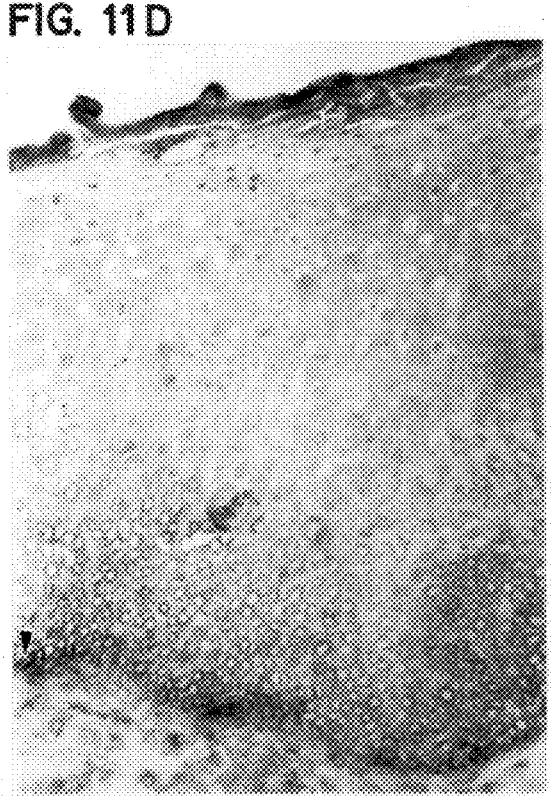

Comparison of Transferrin Receptor Expression in Psoriasis, Exfoliative Dermatitis and Non-Psoriasiform Controls. To evaluate the role of phosphorylase kinase in cell cycling, the expression of transferrin receptors (TRR) on keratinocytes was used as a marker for cells capable of undergoing DNA synthesis, i.e. cycling cells (S. Eriksson et al. (1984), supra; J. Laskey et al. (1988), supra; L. M. Neckers et al. (1983), supra). This premise is based on the fact that transferrin receptors are involved in cell proliferation since iron is required by ribonucleotide reductase for the S phase of DNA synthesis (E. J. O'Keefe & R. E. Payne, "Modulation of Epidermal Growth Factor-Receptor of Human Keratinocytes by Calcium Ion," *J. Invest. Dermatol.* 81:231–235 (1983)) in cycling cells and increases in TRR induction on cycling cells have been shown to precede increases in DNA synthesis (S. Eriksson et al. (1984), supra; L. M. Neckers et al. (1983), supra), and on observations that transferrin supports cell proliferation by supplying iron for DNA synthesis (O. Baadsgaard et al. (1990), supra) and transferrin receptor (TRR) induction is required for DNA synthesis (J. T. Elder et al. (1990), supra). Increased transferrin receptor (TRR) expression on keratinocytes/rete peg was observed in active psoriatic lesions (FIG. 11a) with 68.5%±11.4% TRR+ keratinocytes. The rete pegs demonstrated 28.3%±6.5% TRR+ keratinocytes in exfoliative dermatitis (FIG. 11b), 9.6%±3.2% TRR+ keratinocytes in healing psoriasis (FIG. 11c), and 10.1%±2.4% TRR+ keratinocytes in non-psoriasiform lesions (FIG. 11d).

Correlation of Phosphorylase Kinase Activity with Transferrin Receptor Expression on Keratinocytes. Phosphorylase kinase activity correlated closely and positively with transferrin receptor (TRR) expression in all four groups. In active psoriasis, the r value was 0.87 (FIG. 12A). In the other 3 groups, which had lower phosphorylase kinase activity (FIGS. 12B–D), the r values were 0.88 in exfoliative dermatitis, 0.98 in healing psoriasis and 0.96 in the skin cancer/eczema groups respectively.

In summary, phosphorylase kinase activity (units/mg protein) was 27.9±11.4 (SD) in involved skin of active psoriasis, 11.3±4.6 in exfoliative dermatitis, 4.1±2.4 in healing psoriasis, and 5.0±2.2 in eczemas and skin cancers. Enzyme activity was significantly higher in psoriasiform hyperplasia than non-psoriasiform hyperplasia. It correlated with the pool of cycling cells as determined by the percentage of keratinocytes expressing transferrin receptors (TRR) per rete ridge, with significantly greater TRR receptor expression in psoriasiform hyperplastic lesions (active psoriasis: 68.5±6.1 (SD); exfoliative dermatitis: 28.3±6.5) compared to non-psoriasiform lesions (healing psoriasis: 7.9±4.7; skin cancers and eczemas: 10.1±2.4). Phosphorylase kinase activity also correlated with calmodulin levels but not with cAMP levels. This data suggests that increased activity of phosphorylase kinase, a calmodulin-containing enzyme, is involved in cell cycling and psoriasiform hyperplasia. Therefore, this data supports the use of phosphorylase kinase inhibitors, calmodulin inhibitors, calcium-channel blockers, and other agents to reduce the activity of phosphorylase kinase in the treatment of psoriasis.

ADVANTAGES OF THE PRESENT INVENTION

The present invention provides an improved method of treating psoriasis by controlling the proliferation and terminal differentiation of psoriatic epidermis through the activity of epidermal phosphorylase kinase. By modulating the activity of phosphorylase kinase at several points at once, the method of the present invention can better compensate for overproduction of the enzyme that might occur in psoriasis and provides more efficient control of its activity than does the use of only one drug having an effect on the activity of phosphorylase kinase. The method does not interfere with other systemic or topical treatments for psoriasis such as the use of tars. The method offers improved long-term control for psoriasis, and may also be of value in other epidermal disorders involving hyperproliferation and excessive cell cycling.

Although the present invention has been described in considerable detail with regard to certain preferred versions thereof, other versions are possible. Therefore, the spirit and scope of the appended claims should not be limited to the descriptions of the preferred versions contained herein.

I claim:

1. A method for inhibiting proliferation and terminal differentiation of psoriatic epidermal cells comprising the step of contacting the psoriatic epidermal cells with curcumin administered in a dose and by a route selected from the group consisting of (a) oral administration from 250 mq to 2 g daily and (b) a topical gel in the concentration of 0.1% to 10%, together with one to four additional compounds, each additional compound being selected from the group consisting of:

(i) $1\alpha,25$-dihydroxy vitamin $D_3$ in the form of an 0.005% ointment;

(ii) etretinate administered in a dose of 25 mg from one to three times daily;

(iii) diltiazem administered at a dose of 60 mg three times daily; and (iv) anthralin administered in an ointment or paste in a concentration of from about 0.1% to about 3% once or twice daily.

2. The method of claim 1 wherein the additional compound is $1\alpha,25$-dihydroxy vitamin $D_3$ in the form of an 0.005% ointment.

3. The method of claim 1 wherein the additional compound is etretinate administered in a dose of 25 mg from one to three times daily.

4. The method of claim 1 wherein the additional compound is anthralin administered in an ointment or paste in a concentration of from about 0% to about 3% once or twice daily.

5. The method of claim 1 wherein the additional compound is diltiazem administered at a dose of 60 mg three times daily.

\* \* \* \* \*

Disclaimer 5,925,376 - Madalene C. Y. Heng, Northridge, Calif. METHOD FOR TREATING PSORIASIS USING SELECTED PHOSPHORYLASE KINASE INHIBITOR AND ADDITIONAL COMPOUNDS. Patent dated July 20, 1999. Disclaimer filed January 3, 2000, by the inventor.

Hereby enters this disclaimer to claims 1, 3, and 4 of said patent.

*(Official Gazette, February 8, 2000)*

(12) REEXAMINATION CERTIFICATE (4294th)
United States Patent
Heng

(10) Number: US 5,925,376 C1
(45) Certificate Issued: Mar. 20, 2001

(54) METHOD FOR TREATING PSORIASIS USING SELECTED PHOSPHORYLASE KINASE INHIBITOR AND ADDITIONAL COMPOUNDS

(75) Inventor: Madalene C. Y. Heng, 17632 Vincennes St., Northridge, CA (US) 91325

(73) Assignee: Madalene C. Y. Heng, Northridge, CA (US)

Reexamination Request:
No. 90/005,533, Nov. 1, 1999

Reexamination Certificate for:
Patent No.: 5,925,376
Issued: Jul. 20, 1999
Appl. No.: 08/518,991
Filed: Aug. 24, 1995

Disclaimer of Claims 1, 3 and 4 filed Jan. 3, 2000 (1231 O.G. 40)

Related U.S. Application Data

(63) Continuation-in-part of application No. 08/179,167, filed on Jan. 10, 1994, now abandoned.

(51) Int. Cl.$^7$ .............................. A61K 9/20; A61K 9/06
(52) U.S. Cl. .................. 424/451; 514/679; 514/863; 514/944; 514/962; 514/969; 514/937; 514/886
(58) Field of Search ................... 424/472, 195.1, 424/451, 464; 514/731, 886, 863, 944, 937, 962, 969, 679

(56) References Cited

U.S. PATENT DOCUMENTS 5,401,777 * 3/1995 Ammon et al. ............... 514/731

OTHER PUBLICATIONS

714, The Merck Index, Eleventh Edition, 1989.*

* cited by examiner

Primary Examiner—James M. Spear

(57) ABSTRACT

An improved method of treating psoriasis involves controlling the enhanced proliferation and terminal differentiation of psoriatic epidermis through the activity of epidermal phosphorylase kinase. In general, the method involves contacting psoriatic epidermal cells with a combination of substances affecting the activity of phosphorylase kinase. The combination can be: (1) a calmodulin inhibitor together with a stimulator of cAMP-dependent protein kinase II, (2) a calmodulin inhibitor together with a calcium channel blocker; (3) a stimulator of cAMP-dependent protein kinase II together with a calcium channel blocker; or (4) a calmodulin inhibitor together with a calcium channel blocker and a stimulator of cAMP-dependent protein kinase II. Alternatively, a selective phosphorylase kinase inhibitor such as curcumin can be administered, alone or with an agent such as vitamin $D_3$ or an analogue thereof, etretinate, diltiazem, or anthralin. The invention also includes pharmaceutical compositions.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3 and 4 were previously disclaimed.

Claims 2 and 5 are determined to be patentable as amended.

2. [The] *A* method [of claim 1] *for inhibiting proliferation and terminal differentiation of psoriatic epidermal cells comprising the step of contacting the psoriatic epidermal cells with curcumin administered in a dose and by a route selected from the group consisting of (a) oral administration from 250 mg to 2 g daily and (b) a topical gel in the concentration of 0.1% to 10%, together with an additional compound,* wherein the additional compound is 1α,25-dihydroxy vitamin $D_3$ in the form of an 0.005% ointment.

5. [The] *A* method [of claim 1] *for inhibiting proliferation and terminal differentiation of psoriatic epidermal cells comprising the step of contacting the psoriatic epidermal cells with curcumin administered in a dose and by a route selected from the group consisting of (a) oral administration from 250 mg to 2 g daily and (b) a topical gel in the concentration of 0.1% to 10%, together with an additional compound,* wherein the additional compound is diltiazem administered at a dose of 60 mg three times daily.

* * * * *